US012757908B2

(12) United States Patent
Mao

(10) Patent No.: US 12,757,908 B2
(45) Date of Patent: Oct. 13, 2026

(54) FOOD PRODUCTS STABLE AT AMBIENT TEMPERATURE

(71) Applicant: INTERNATIONAL N&H DENMARK ApS, Kongens Lyngby (DK)

(72) Inventor: Yuejian Mao, Shanghai (CN)

(73) Assignee: International N&H Denmark ApS, Kongens Lyngby (DK)

( * ) Notice: Subject to any disclaimer, the term of this patent is extended or adjusted under 35 U.S.C. 154(b) by 929 days.

(21) Appl. No.: 17/260,814

(22) PCT Filed: Jul. 16, 2019

(86) PCT No.: PCT/EP2019/069064
§ 371 (c)(1),
(2) Date: Jan. 15, 2021

(87) PCT Pub. No.: WO2020/016203
PCT Pub. Date: Jan. 23, 2020

(65) Prior Publication Data

US 2021/0274799 A1 Sep. 9, 2021

(30) Foreign Application Priority Data

Jul. 17, 2018 (WO) ................ PCT/CN2018/095982

(51) Int. Cl.
*A23C 9/123* (2006.01)
*C12N 1/205* (2026.01)
*C12R 1/25* (2006.01)

(52) U.S. Cl.
CPC ............ *A23C 9/1234* (2013.01); *C12N 1/205* (2021.05); *A23V 2400/169* (2023.08); *C12R 2001/25* (2021.05)

(58) Field of Classification Search
CPC ........................................................ A23C 9/12
See application file for complete search history.

(56) References Cited

U.S. PATENT DOCUMENTS 4,425,366 A 1/1984 Sozzi et al.
2003/0031756 A1 2/2003 Boufassa et al.
2012/0156327 A1* 6/2012 Robichon ............ A23C 9/1238 426/43
2014/0113028 A1 4/2014 Bruinenberg
(Continued)

FOREIGN PATENT DOCUMENTS

CN 1953667 A 4/2007
CN 101273736 A 10/2008
(Continued)

OTHER PUBLICATIONS

Gao et al. (CN 102747009) Machine Translation Oct. 24, 2012. (Year: 2012).*
(Continued)

*Primary Examiner* — Felicia C Turner

(57) ABSTRACT

The application is directed to a process for manufacturing a food product stable at ambient temperature based on the inoculation of a food product with stable lactic acid bacteria able to maintain viability and to slightly decrease pH when stored at ambient temperature. The invention is also directed to the use of these stable lactic acid bacteria for inoculation in a food product.

13 Claims, 7 Drawing Sheets

Specification includes a Sequence Listing.

(56) References Cited

U.S. PATENT DOCUMENTS

| | | | | |
|---|---|---|---|---|
| 2014/0220177 | A1* | 8/2014 | Druesne | A23C 9/123 435/252.3 |
| 2017/0172161 | A1 | 6/2017 | Nag et al. | |

FOREIGN PATENT DOCUMENTS

| | | | | |
|---|---|---|---|---|
| CN | 105325541 | A | 2/2016 | |
| CN | 107118975 | A | 9/2017 | |
| CN | 109619180 | A | 4/2019 | |
| WO | 2005089560 | A1 | 9/2005 | |
| WO | WO-2017194650 | A1 * | 11/2017 | A23C 9/12 |
| WO | 2019063676 | A1 | 4/2019 | |

OTHER PUBLICATIONS

Chen et al., Potential probiotic characterization of Lactobacillus reuteri from traditional Chinese highland barley wine and application for room-temperature-storage drinkable yogurt, J. Dairy Sci., Jul. 2018, 101(7):5780-5788.
Chuah et al., Stability assessment and improvement of a Lactobacillus plantarum mutant with low post-fermentation acidification characteristics, J. Dairy Sci., Sep. 2020, 103(9):7898-7907.
Jaichumjai et al., Isolation and characterization of acid-sensitive Lactobacillus plantarum with application as starter culture for Nham production, Food Microbiology, Sep. 2010, 27(6):741-748.
Semic et al., Effects of Increasing Sourness of Bread Dough on Bread Quality, 5th International Congress Flour-Bread '09, 7th Croatian Congress of Cereal Technologists, Oct. 2010, 416-424.
International Search Report, International Application No. PCT/EP2019/069064, mailed Nov. 8, 2019, 5 pgs.
Cai, Yimin et al., *Lactobacillus nasuensis* sp. nov., a lactic acid bacterium isolated from silage, and emended description of the genus *Lactobacillus*, International Journal of Systematic and Evolutionary Microbiology, 2012, pp. 1140-1144, vol. 62.
Jaichumjai, Pornpan et al., Isolation and characterization of acid-sensitive Lactobacillus plantarum with application as starter culture for Nham production, Food Microbiology, 2010, pp. 741-748, vol. 27.
Salvetti, Elisa et al., The Genus *Lactobacillus*: A Taxonomic Update, Probiotics & Antimicro. Prot, 2012, pp. 217-226, vol. 4.
Semic, A. et al., Effects of Increasing Sourness of Bread Dough on Bread Quality, 7th Croatian Congress of Cereal Technologists, Oct. 30, 2010, pp. 416-424.
International Search Report and Written Opinion—PCT/EP2019/069064—mailed Nov. 8, 2018.
Kamimura, Naofumi et al., Bacterial catabolism of lignin-derived aromatics: New findings in a recent decade Environmental Microbiology Reports, 2017, pp. 679-705, vol. 9(6).
Lim, Ji Youn et al., A brief overview of *Escherichia coli* O157:H7 and its plasmid O157, j Microbiol Biotechnol., Jan. 2010, pp. 5-14, vol. 20 (1).
Derkx, P.M. et al., The art of strain improvement of industrial lactic acid bacteria without the use of recombinant DNA technology, Microbial Cell Factories, 2014, 13 (Suppl 1), S5.

* cited by examiner

A.

B.

A.

B.

A.

B.

SEQUENCE LISTING

<160> NUMBER OF SEQ ID NOS: 5

<210> SEQ ID NO 1
<211> LENGTH: 6453
<212> TYPE: DNA
<213> ORGANISM: Lactobacillus plantarum

<400> SEQUENCE: 1

```
gtgggtgatc cagttcctac agtcaaattc cttggactga cgtttaatat cgcgaatgac     60

atctcagtaa ttgtgacttg tctgattgtt ttcttgtttg tttttttact ttcgcgacat    120

ttaacaatga agcccaaggg tggacaaaat gtgctggagt ggctcatcga gttcacgaat    180

ggcattgtca aagggtcgat caagggtaac gaagcgtcta acttcggttt gtacgcattt    240

acattgtttc tctttatctt catcgctaac caacttggat tgttcattca cgttcaggtc    300

gggcagtata cgtatctgaa gagtccaacc gccgatccga ttgtgacttt gacgttatcg    360

tttatgaccg ttgcacttgc acatgctgcg ggtgttcgta agaaaggtat gggtggttat    420

ttgaaagaat acacacaacc ttttgctgtt ttctcggttg ttaacgtctt tgaacaattt    480

accgatttcc taactttagg tcttcggctg ttcgggaaca tctttgctgg tgaaatgtta    540

ctaacgaagg ttgctgattt ggcaaagagc aacggttggt tgagctatgt ttactcattt    600

ccaattgaac tcttatggca aggtttctca gtgtttatcg ggagcattca agcgttcgtg    660

ttcgtaacct tgacttcagt ttatatttct cagaaggtta acgacgagga ataatttcta    720

gtttttaat tttaaggagg atacacagat tatgggagca attgctgcag gtattgctat    780

gtgtggtgcc gctataggtg ctggtattgg taacggtttg gttatttcta agatgcttga    840

agggatggcc cgtcaaccag aattatctgg tcaattacgg actaacatgt tcatcggtgt    900

tgggttggtc gaatcaatgc ctataatttc cttcgttgtt gctttgatgg ttatgaacaa    960

gtaatcattg gtcaacgagt tcattttaat gaaaatgaaa gaaggaggtg tcattagatg   1020

ctctcgcatt taattatcgg tgcatccggt ctctaccttg gtgatatgtt gtttatcggg   1080

attagcttta ttgttttgat ggcattgatc tctgttgttg cttggaagcc catcacaaaa   1140

atgatggctg atcgagccga caagattgcg aacgacattg attcagcaca aaagtctcgg   1200

caagaagcga gtgacttagc tgatcaacgg cgtgatgcgc tatcacactc tcgcgctgaa   1260

gcgagtgaaa ttgtcgctga cgcgaaaaag agtggcgaaa agcaacggtc aagtatcatt   1320

gccgatgcgc aaaacgaagc aacgcagtat aaacaaaatg cgcgtaagga tattgaacag   1380

gagcgtcaag atgccttgaa gaacgtccaa tcagacgtcg ctgacatttc gattgcgatt   1440

gctacgaaga ttattaagaa gcaattggat ccggaaggcc aacaggcatt aattaattcg   1500

tatattgaag ggttgggaaa gcatgagtct tgataatctt acaattgcaa gtcgttattc   1560

aaaggcactc tttgaacttg cagttgaaaa agatcagacc gaagcattcc tggccgagtt   1620

aaagcaatta cggcaagtct ttgtcgacaa cccgcaattg gcagaggtcc tctcaggatc   1680

attgcttccg gttgatcaaa aacagacaac gttgtcaact ttgactgacc acgcttcaga   1740

atacattaaa aactttattc aaatgttgta tgattacggc cgcatgtcga acttagttgg   1800

cattgttgac gcgtttgaag cacgtttcga tgagagtcgc aaaatagtgc atgccgaagt   1860

aacgtctgcg gtcaagttgt cagatgagca agctgatgca atcgcaaagg cattcgccaa   1920

acgtgttggg gccaatcagg ttgttttgtc acgtaaagtc gatgaagcaa tcattggcgg   1980

tgtaattgtg aagtcaaata atcaaacgtt tgatggtagc gttgcgttac aactaacgaa   2040

tttaagacga gcactcatca acaattagtt tacgaagagg tgaaactttt atgagcatta   2100
```

```
aatctgaaga aatcagtgct ctaatcaaac aacaattaga aagttatcaa actgagctct   2160
cagttgctga aaccggtact gtcacctacg ttggtgatgg gatcgcccgt gctcacggac   2220
tcgacaacgc cttacaaggt gaattactcg aattcagtaa cggagtttac gggatggtac   2280
aaaacctcga aagcaacgat gttggtatcg ttgttttagg ggattttgat ggtattcgtg   2340
aaggcgatac tgttaagcgg actggccgca tcatggaagt tccagtcggt gacgccatga   2400
ttggccgggt cgttaaccca ttaggtcaac cagttgacgg ttcaggtgag attaagacca   2460
cgaatacgcg gccaatcgaa cataaagctc ctggtattat gcaacggcaa tcagttagcg   2520
aaccacttca aactgggatc aaggccattg atgccttagt tccaattggt cggggccaac   2580
gtgaattgat tatcggtgac cgtaagactg ggaagacgtc cgttgccatt gatgccattt   2640
tgaaccaaaa ggaccaagac atgatttgtg tctacgttgc aatcggtcaa aaggactcaa   2700
ctgtacgggc ccaagttgaa acgttgaaga agttaggtgc gatggactac acaatcgttg   2760
taactgccgg acctgctgaa ccagcgccat tactgtactt agctccttat gctggggcag   2820
cgatgggtga agaatttatg atgaacggca agcacgtttt gatcgtctat gatgaccttt   2880
caaagcaagc aacggcttac cgtgaacttt ccttgatcct ccgtcgtcct ccaggtcgtg   2940
aagcttatcc tggggatgtc ttctacttgc actcacggtt actcgaacgg gctgccaagt   3000
tgagcgatga attgggtggc ggttcaatga cggccttacc aattatcgaa acgcaagctg   3060
gggatatttc ggcttatatt ccaactaacg ttatttcaat caccgatggg caaatcttct   3120
tggatagtga ttcattctat tcaggtgtgc ggccagcgat tgatgccggg gcctctgttt   3180
cccgggttgg tggggatgcg caaattaaag cgatgaagtc cgttgccggg accttgcgtc   3240
ttgacttggc ttcttatcgt gaattggaat ccttctcaca attcggttct gacttggatg   3300
ctgcaaccca agcgaaatta aatcgtgggc aacggatcgt tgaagtctta aaacaacctg   3360
ttcattcacc attgaaggtc gaagaacaag taatgatttt atatgctttg accaacggtt   3420
atttggataa agtggcagtt gatgatattg cccgttacca aagtgaattg tttgaattta   3480
ttcatgctag tcatcaggac ctctttgata cgattttggc aaccaagaag ttaccagaag   3540
ctgataagat gaatggggcc ttagatgcgt ttgcagaaca attccagcca accgctgccg   3600
ctgcgaagta gttatggctg aaaaggatgg tgagtagtgc atggcagaat cattaatgga   3660
tgtcaagcgc cgaattgact caacaaagaa gactcatcaa attacgtcgg caatgcaaat   3720
ggtctcaact tcaaaattga accagattca aaagcatacc agcacgtatc aggtgtacgc   3780
ttctaaagtt gaaagcatcg tttcacatct tgccaaagct catctgatgt cagcaagtgc   3840
cggtgttgct aacagtaatt cgaacacgat ttcagttagt gaattgctcg cgcaacgccc   3900
cgttaaaaag actggtttat tggtgatcac ttcggaccgt ggcctcgttg gtagttacaa   3960
cagtaacgtg ttgaaacaga ctaacgattt catgcggacg cacaaggttg atgccgataa   4020
cgcagtcgtt ttggcggttg gtggcactgg tgcggatttc tataaaaaga acgggttaaa   4080
cgtggcttat gagtaccgcg gcgtctctga tgtcccaact tttaaagagg ttcgtgaaat   4140
cgttaagaca gtcacatcaa tgtaccacaa cgaagtcttt gatgaacttt acgtcttcta   4200
caaccacttt attaatcggc tctcttctgg ttttcgggcc gttaagatgt taccgatctc   4260
cgaagagacc tttgaacaaa gtgagtcaga taatcgtaaa gccaaggata gccgggtaga   4320
tgtcggtccc gagtatgaaa tggaaccgtc agaagaagcc attttgtcgg ccgtgttgcc   4380
acaatatgct gaaagcttgg tttatggtgc aatcttggat gccaagactg ctgaacatgc   4440
```

ttcgtcgtca accgcgatga aggctgcatc agataacgct ggcgatttaa tcgataaatt 4500
aaatctgaaa tataaccgtg cgcgtcaagc tgctattacc actgaaatca ctgaaatcac 4560
tggtggtttg gttgcgcaag aataacgaag tgggaggaat taacgactaa tgagtacagg 4620
taaagttgta caagttattg gacccgttgt tgacgttgaa ttctctctaa acgataagtt 4680
acccgatatt aataacgcct tgatcattca gaaggacaac gatgacactt taacggtgga 4740
agtatcgttg gaattaggtg atggggttgt tcggaccgtc gcgatggatg gtacggatgg 4800
cttgcgccgg ggaatgacag ttgaagacac tggttcttca attactgttc ccgttggtaa 4860
agagacgtta ggccgggtct tcaacgtttt aggggaaacc attgatggtg gtccagaatt 4920
cggtccagac gcagaacgta acccgattca tcgggatgcg cctaaatatg atgaattaac 4980
gaccagtact gaagtattgg aaactggaat taaagttatt gacctcttag caccttatgt 5040
tcgtggtggt aagattgggt tgttcggtgg tgccggtgtt ggtaaaactg ttttaatcca 5100
ggaattaatt cataacattg cccaagaaca taacgggatt tccgtgttta ccggtgttgg 5160
tgaacggacg cgtgaaggga atgaccttta cttcgaaatg aaggcttccg gcgttttgaa 5220
gaataccgcc atggtttatg gtcaaatgaa cgaaccacct ggtgcccgga tgcgggtggc 5280
cttgaccggt ttgacgattg cggaatactt ccgtgatgtt caaggtcaag acgtgttgtt 5340
attcatcgac aatatcttcc ggttcacgca agctggttct gaagtttccg ccttacttgg 5400
tcggattcct tcagccgttg gttaccaacc aaccttagcc actgaaatgg gtcaattaca 5460
agaacggatc acttctacca agaaggggtc agttacttcg attcaagccg tttatgtacc 5520
tgccgatgat tataccgacc cggcacctgc aacgactttc gcccatttgg atgcgacgac 5580
caacttggaa cgttctttga cggaacaagg gatctaccca gccgttgacc cattagcttc 5640
ttcttcaatc gctctggacc catcaatcgt gggcgaagaa cattatcaag ttgcaacgga 5700
agttcaacgg gtcttgcaac gttatcgtga attgcaagat attatctcga ttttagggat 5760
ggatgaatta tctgacgaag aaaagacaac tgttgcgcgt gcacggcgga ttcaattctt 5820
cttgtcacaa aacttcttcg ttgccgaaaa ctttacgggc caacctggtt cgtatgtgcc 5880
aatcaacgat accatcaagg gcttcaaaga aattcttgaa ggtaaatatg atgacctacc 5940
agaagacgca ttccgtcaag ttggtaagat cgacgacgtg gtcgaaaaag cgaaatcgat 6000
ggtaactgat taggaggggt ttacatggct gacaatgcaa aatcattaac cgttagcatc 6060
gtaactccag acggtcaggt ctatgagaat aagacgccaa tgttgatcgt gcgaacgatt 6120
gacggcgaac tcggaatttt gccgaaccat attcctgtga ttgcatcgct tgcaatcgat 6180
gaggttcgga tcaagcaact tgaaagtgat caggaagatg acgaaattgc cgttaatggt 6240
ggttttgttg agttcagtaa taatacggca acgattgttg ccgatagtgc tgaacgtcag 6300
aatgacattg acgttgctcg agctgaaaat gcacggaaac gcgctgaaac acggattcaa 6360
aatgcccaac aaaagcacga tgatgctgag ttggcgcggg cccaagtcgc tttgcggcgt 6420
gccatgaacc gtttgaatgt tgctcggcat taa 6453

<210> SEQ ID NO 2
<211> LENGTH: 1521
<212> TYPE: DNA
<213> ORGANISM: Lactobacillus plantarum

<400> SEQUENCE: 2
atgagcatta aatctgaaga aatcagtgct ctaatcaaac aacaattaga aagttatcaa 60
actgagctct cagttgctga aaccggtact gtcacctacg ttggtgatgg gatcgcccgt 120

```
gctcacggac tcgacaacgc cttacaaggt gaattactcg aattcagtaa cggagtttac    180

gggatggtac aaaacctcga aagcaacgat gttggtatcg ttgttttagg ggattttgat    240

ggtattcgtg aaggcgatac tgttaagcgg actggccgca tcatggaagt tccagtcggt    300

gacgccatga ttggccgggt cgttaaccca ttaggtcaac cagttgacgg ttcaggtgag    360

attaagacca cgaatacgcg gccaatcgaa cataaagctc ctggtattat gcaacggcaa    420

tcagttagcg aaccacttca aactgggatc aaggccattg atgccttagt tccaattggt    480

cggggccaac gtgaattgat tatcggtgac cgtaagactg ggaagacgtc cgttgccatt    540

gatgccattt tgaaccaaaa ggaccaagac atgatttgtg tctacgttgc aatcggtcaa    600

aaggactcaa ctgtacgggc ccaagttgaa acgttgaaga agttaggtgc gatggactac    660

acaatcgttg taactgccgg acctgctgaa ccagcgccat tactgtactt agctccttat    720

gctggggcag cgatgggtga agaatttatg atgaacggca agcacgtttt gatcgtctat    780

gatgaccttt caaagcaagc aacggcttac cgtgaacttt ccttgatcct ccgtcgtcct    840

ccaggtcgtg aagcttatcc tggggatgtc ttctacttgc actcacggtt actcgaacgg    900

gctgccaagt tgagcgatga attgggtggc ggttcaatga cggccttacc aattatcgaa    960

acgcaagctg ggatatttc ggcttatatt ccaactaacg ttatttcaat caccgatggg   1020

caaatcttct tggatagtga ttcattctat tcaggtgtgc ggccagcgat tgatgccggg   1080

gcctctgttt cccgggttgg tggggatgcg caaattaaag cgatgaagtc cgttgccggg   1140

accttgcgtc ttgacttggc ttcttatcgt gaattggaat ccttctcaca attcggttct   1200

gacttggatg ctgcaaccca agcgaaatta aatcgtgggc aacggatcgt tgaagtctta   1260

aaacaacctg ttcattcacc attgaaggtc gaagaacaag taatgatttt atatgctttg   1320

accaacggtt atttggataa agtggcagtt gatgatattg cccgttacca aagtgaattg   1380

tttgaattta ttcatgctag tcatcaggac ctctttgata cgattttggc aaccaagaag   1440

ttaccagaag ctgataagat gaatggggcc ttagatgcgt ttgcagaaca attccagcca   1500

accgctgccg ctgcgaagta g                                              1521
```

<210> SEQ ID NO 3
<211> LENGTH: 506
<212> TYPE: PRT
<213> ORGANISM: Lactobacillus plantarum

<400> SEQUENCE: 3

```
Met Ser Ile Lys Ser Glu Glu Ile Ser Ala Leu Ile Lys Gln Gln Leu
1               5                   10                  15

Glu Ser Tyr Gln Thr Glu Leu Ser Val Ala Glu Thr Gly Thr Val Thr
            20                  25                  30

Tyr Val Gly Asp Gly Ile Ala Arg Ala His Gly Leu Asp Asn Ala Leu
        35                  40                  45

Gln Gly Glu Leu Leu Glu Phe Ser Asn Gly Val Tyr Gly Met Val Gln
    50                  55                  60

Asn Leu Glu Ser Asn Asp Val Gly Ile Val Val Leu Gly Asp Phe Asp
65                  70                  75                  80

Gly Ile Arg Glu Gly Asp Thr Val Lys Arg Thr Gly Arg Ile Met Glu
                85                  90                  95

Val Pro Val Gly Asp Ala Met Ile Gly Arg Val Val Asn Pro Leu Gly
            100                 105                 110

Gln Pro Val Asp Gly Ser Gly Glu Ile Lys Thr Thr Asn Thr Arg Pro
```

```
        115                 120                 125

Ile Glu His Lys Ala Pro Gly Ile Met Gln Arg Gln Ser Val Ser Glu
    130                 135                 140

Pro Leu Gln Thr Gly Ile Lys Ala Ile Asp Ala Leu Val Pro Ile Gly
145                 150                 155                 160

Arg Gly Gln Arg Glu Leu Ile Ile Gly Asp Arg Lys Thr Gly Lys Thr
                165                 170                 175

Ser Val Ala Ile Asp Ala Ile Leu Asn Gln Lys Asp Gln Asp Met Ile
            180                 185                 190

Cys Val Tyr Val Ala Ile Gly Gln Lys Asp Ser Thr Val Arg Ala Gln
        195                 200                 205

Val Glu Thr Leu Lys Lys Leu Gly Ala Met Asp Tyr Thr Ile Val Val
    210                 215                 220

Thr Ala Gly Pro Ala Glu Pro Ala Pro Leu Leu Tyr Leu Ala Pro Tyr
225                 230                 235                 240

Ala Gly Ala Ala Met Gly Glu Glu Phe Met Met Asn Gly Lys His Val
                245                 250                 255

Leu Ile Val Tyr Asp Asp Leu Ser Lys Gln Ala Thr Ala Tyr Arg Glu
            260                 265                 270

Leu Ser Leu Ile Leu Arg Arg Pro Pro Gly Arg Glu Ala Tyr Pro Gly
        275                 280                 285

Asp Val Phe Tyr Leu His Ser Arg Leu Leu Glu Arg Ala Ala Lys Leu
    290                 295                 300

Ser Asp Glu Leu Gly Gly Gly Ser Met Thr Ala Leu Pro Ile Ile Glu
305                 310                 315                 320

Thr Gln Ala Gly Asp Ile Ser Ala Tyr Ile Pro Thr Asn Val Ile Ser
                325                 330                 335

Ile Thr Asp Gly Gln Ile Phe Leu Asp Ser Asp Ser Phe Tyr Ser Gly
            340                 345                 350

Val Arg Pro Ala Ile Asp Ala Gly Ala Ser Val Ser Arg Val Gly Gly
        355                 360                 365

Asp Ala Gln Ile Lys Ala Met Lys Ser Val Ala Gly Thr Leu Arg Leu
    370                 375                 380

Asp Leu Ala Ser Tyr Arg Glu Leu Glu Ser Phe Ser Gln Phe Gly Ser
385                 390                 395                 400

Asp Leu Asp Ala Ala Thr Gln Ala Lys Leu Asn Arg Gly Gln Arg Ile
                405                 410                 415

Val Glu Val Leu Lys Gln Pro Val His Ser Pro Leu Lys Val Glu Glu
            420                 425                 430

Gln Val Met Ile Leu Tyr Ala Leu Thr Asn Gly Tyr Leu Asp Lys Val
        435                 440                 445

Ala Val Asp Asp Ile Ala Arg Tyr Gln Ser Glu Leu Phe Glu Phe Ile
    450                 455                 460

His Ala Ser His Gln Asp Leu Phe Asp Thr Ile Leu Ala Thr Lys Lys
465                 470                 475                 480

Leu Pro Glu Ala Asp Lys Met Asn Gly Ala Leu Asp Ala Phe Ala Glu
                485                 490                 495

Gln Phe Gln Pro Thr Ala Ala Ala Ala Lys
            500                 505

<210> SEQ ID NO 4
<211> LENGTH: 1521
<212> TYPE: DNA
<213> ORGANISM: Lactobacillus plantarum
```

<400> SEQUENCE: 4

```
atgagcatta aatctgaaga aatcagtgct ctaatcaaac aacaattaga aagttatcaa     60
actgagctct cagttgctga aaccggtact gtcacctacg ttggtgatgg gatcgcccgt    120
gctcacggac tcgacaacgc cttacaaggt gaattactcg aattcagtaa cggagtttac    180
gggatggtac aaaacctcga aagcaacgat gttggtatcg ttgttttagg ggattttgat    240
ggtattcgtg aaggcgatac tgttaagcgg actggccgca tcatggaagt tccagtcggt    300
gacgccatga ttggccgggt cgttaaccca ttaggtcaac cagttgacgg ttcaggtgag    360
attaagacca cgaatacgcg gccaatcgaa cataaagctc ctggtattat gcaacggcaa    420
tcagttagcg aaccacttca aactgggatc aaggccattg atgccttagt tccaattggt    480
cggggccaac gtgaattgat tatcgatgac cgtaagactg ggaagacgtc cgttgccatt    540
gatgccattt tgaaccaaaa ggaccaagac atgatttgtg tctacgttgc aatcggtcaa    600
aaggactcaa ctgtacgggc ccaagttgaa acgttgaaga agttaggtgc gatggactac    660
acaatcgttg taactgccgg acctgctgaa ccagcgccat tactgtactt agctccttat    720
gctggggcag cgatgggtga agaatttatg atgaacggca agcacgtttt gatcgtctat    780
gatgaccttt caaagcaagc aacggcttac cgtgaacttt ccttgatcct ccgtcgtcct    840
ccaggtcgtg aagcttatcc tggggatgtc ttctacttgc actcacggtt actcgaacgg    900
gctgccaagt tgagcgatga attgggtggc ggttcaatga cggccttacc aattatcgaa    960
acgcaagctg gggatatttc ggcttatatt ccaactaacg ttatttcaat caccgatggg   1020
caaatcttct tggatagtga ttcattctat tcaggtgtgc ggccagcgat tgatgccggg   1080
gcctctgttt cccgggttgg tggggatgcg caaattaaag cgatgaagtc cgttgccggg   1140
accttgcgtc ttgacttggc ttcttatcgt gaattggaat ccttctcaca attcggttct   1200
gacttggatg ctgcaaccca agcgaaatta aatcgtgggc aacggatcgt tgaagtctta   1260
aaacaacctg ttcattcacc attgaaggtc gaagaacaag taatgatttt atatgctttg   1320
accaacggtt atttggataa agtggcagtt gatgatattg cccgttacca aagtgaattg   1380
tttgaattta ttcatgctag tcatcaggac ctctttgata cgattttggc aaccaagaag   1440
ttaccagaag ctgataagat gaatggggcc ttagatgcgt ttgcagaaca attccagcca   1500
accgctgccg ctgcgaagta g                                             1521
```

<210> SEQ ID NO 5
<211> LENGTH: 506
<212> TYPE: PRT
<213> ORGANISM: Lactobacillus plantarum

<400> SEQUENCE: 5

```
Met Ser Ile Lys Ser Glu Glu Ile Ser Ala Leu Ile Lys Gln Gln Leu
1               5                   10                  15

Glu Ser Tyr Gln Thr Glu Leu Ser Val Ala Glu Thr Gly Thr Val Thr
            20                  25                  30

Tyr Val Gly Asp Gly Ile Ala Arg Ala His Gly Leu Asp Asn Ala Leu
        35                  40                  45

Gln Gly Glu Leu Leu Glu Phe Ser Asn Gly Val Tyr Gly Met Val Gln
    50                  55                  60

Asn Leu Glu Ser Asn Asp Val Gly Ile Val Val Leu Gly Asp Phe Asp
65                  70                  75                  80

Gly Ile Arg Glu Gly Asp Thr Val Lys Arg Thr Gly Arg Ile Met Glu
```

-continued

```
                85                  90                  95

Val Pro Val Gly Asp Ala Met Ile Gly Arg Val Val Asn Pro Leu Gly
            100                 105                 110

Gln Pro Val Asp Gly Ser Gly Glu Ile Lys Thr Thr Asn Thr Arg Pro
        115                 120                 125

Ile Glu His Lys Ala Pro Gly Ile Met Gln Arg Gln Ser Val Ser Glu
    130                 135                 140

Pro Leu Gln Thr Gly Ile Lys Ala Ile Asp Ala Leu Val Pro Ile Gly
145                 150                 155                 160

Arg Gly Gln Arg Glu Leu Ile Ile Asp Asp Arg Lys Thr Gly Lys Thr
                165                 170                 175

Ser Val Ala Ile Asp Ala Ile Leu Asn Gln Lys Asp Gln Asp Met Ile
            180                 185                 190

Cys Val Tyr Val Ala Ile Gly Gln Lys Asp Ser Thr Val Arg Ala Gln
        195                 200                 205

Val Glu Thr Leu Lys Lys Leu Gly Ala Met Asp Tyr Thr Ile Val Val
    210                 215                 220

Thr Ala Gly Pro Ala Glu Pro Ala Pro Leu Leu Tyr Leu Ala Pro Tyr
225                 230                 235                 240

Ala Gly Ala Ala Met Gly Glu Glu Phe Met Met Asn Gly Lys His Val
                245                 250                 255

Leu Ile Val Tyr Asp Asp Leu Ser Lys Gln Ala Thr Ala Tyr Arg Glu
            260                 265                 270

Leu Ser Leu Ile Leu Arg Arg Pro Pro Gly Arg Glu Ala Tyr Pro Gly
        275                 280                 285

Asp Val Phe Tyr Leu His Ser Arg Leu Leu Glu Arg Ala Ala Lys Leu
    290                 295                 300

Ser Asp Glu Leu Gly Gly Gly Ser Met Thr Ala Leu Pro Ile Ile Glu
305                 310                 315                 320

Thr Gln Ala Gly Asp Ile Ser Ala Tyr Ile Pro Thr Asn Val Ile Ser
                325                 330                 335

Ile Thr Asp Gly Gln Ile Phe Leu Asp Ser Asp Ser Phe Tyr Ser Gly
            340                 345                 350

Val Arg Pro Ala Ile Asp Ala Gly Ala Ser Val Ser Arg Val Gly Gly
        355                 360                 365

Asp Ala Gln Ile Lys Ala Met Lys Ser Val Ala Gly Thr Leu Arg Leu
    370                 375                 380

Asp Leu Ala Ser Tyr Arg Glu Leu Glu Ser Phe Ser Gln Phe Gly Ser
385                 390                 395                 400

Asp Leu Asp Ala Ala Thr Gln Ala Lys Leu Asn Arg Gly Gln Arg Ile
                405                 410                 415

Val Glu Val Leu Lys Gln Pro Val His Ser Pro Leu Lys Val Glu Glu
            420                 425                 430

Gln Val Met Ile Leu Tyr Ala Leu Thr Asn Gly Tyr Leu Asp Lys Val
        435                 440                 445

Ala Val Asp Asp Ile Ala Arg Tyr Gln Ser Glu Leu Phe Glu Phe Ile
    450                 455                 460
```

-continued

```
His Ala Ser His Gln Asp Leu Phe Asp Thr Ile Leu Ala Thr Lys Lys
465                 470                 475                 480

Leu Pro Glu Ala Asp Lys Met Asn Gly Ala Leu Asp Ala Phe Ala Glu
                485                 490                 495

Gln Phe Gln Pro Thr Ala Ala Ala Ala Lys
            500                 505
```

FOOD PRODUCTS STABLE AT AMBIENT TEMPERATURE

CROSS-REFERENCE TO RELATED APPLICATIONS

This application is a U.S. national stage application under 35 U.S.C. § 371 of International Application No. PCT/EP2019/069064, filed on Jul. 16, 2019, entitled "NEW FOOD PRODUCTS STABLE AT AMBIENT TEMPERATURE," which, in turn, claims priority to PCT/CN2018/095982, filed on Jul. 17, 2018, entitled "NEW FOOD PRODUCTS STABLE AT AMBIENT TEMPERATURE," the contents of which are both incorporated by reference in their entireties.

INCORPORATION BY REFERENCE OF THE SEQUENCE LISTING

The Sequence Listing submitted in an ASCII text file, in accordance with 37 C.F.R. §§ 1.821(c) and (e), is incorporated herein by reference. The text file name is "NB41456WOPCT_Seq_Listing.txt", the date of creation of the text file is Jul. 10, 2018, and the size of the ASCII text file in bytes is 21,785.

FIELD OF THE INVENTION

The application is directed to a process for manufacturing a food product stable at ambient temperature based on the inoculation of a food product with one or more stable lactic acid bacteria able to maintain viability and to slightly decrease pH when stored at ambient temperature. The invention is also directed to the use of these one or more stable lactic acid bacteria for inoculation in a food product.

BACKGROUND TO THE INVENTION

These last years, a trend has emerged for food products, in particular dairy products, containing high level of live bacteria (for their health benefits), which at the same time can be stored at ambient temperature. Indeed, consumers are looking for healthy food products which are easy to be consumed, i.e., easy to be transported and to be stored. Such ambient products are also advantageous in countries where the cold chain during the distribution and storage of food products containing high level of live bacteria is complex, not to say economically or technically impossible.

The two major issues resulting from the storage at ambient temperature of food products containing high level of live bacteria are: (1) the multiplication of the live bacteria in the food product resulting in the production of undesired metabolites which finally impact the quality of the food product (as an example, lactic acid bacteria are able to produce lactic acid at ambient temperature resulting in a non-acceptable pH decrease of the final product such as dairy product), and then (2) the death of the bacteria which are not able to survive in the food matrix at ambient temperature, resulting in the loss of the benefits associated with the bacteria.

Application WO2017/194650 describes *Lactobacillus* strains of the species *paracasei, rhamnosus, fermentum* or *delbrueckii* subsp *bulgaricus* capable of retaining viability in an amount of at least $10^3$ cfu/g (starting from a level of $2.5\times10^7$ cfu/g) and not decreasing the pH of a test product more than 0.8 units, after storage for 150 days (5 months) at 25° C.

However, food producers are looking for means for constantly improving the level of lactic acid bacteria (in particular by reducing the level of viability decrease as compared to the inoculation level) and for reducing the pH decrease in food products, in order to guarantee their customers acceptable bacteria health benefits and a constant food product quality, in particular when the food product is stored at ambient temperature. Moreover, in some countries, such as China, there is a requirement both from producers and consumers to be able to store food products for at least 6 months at ambient temperature, without impacting the characteristics of the food product.

Therefore, there is still a need to identify bacteria which are—when inoculated in a food product—both able to retain a high viability and able to lead to a lesser pH decrease, after storage of this food product at ambient temperature in stricter conditions (at least 6 months).

DETAILED DESCRIPTION

Figure 1:
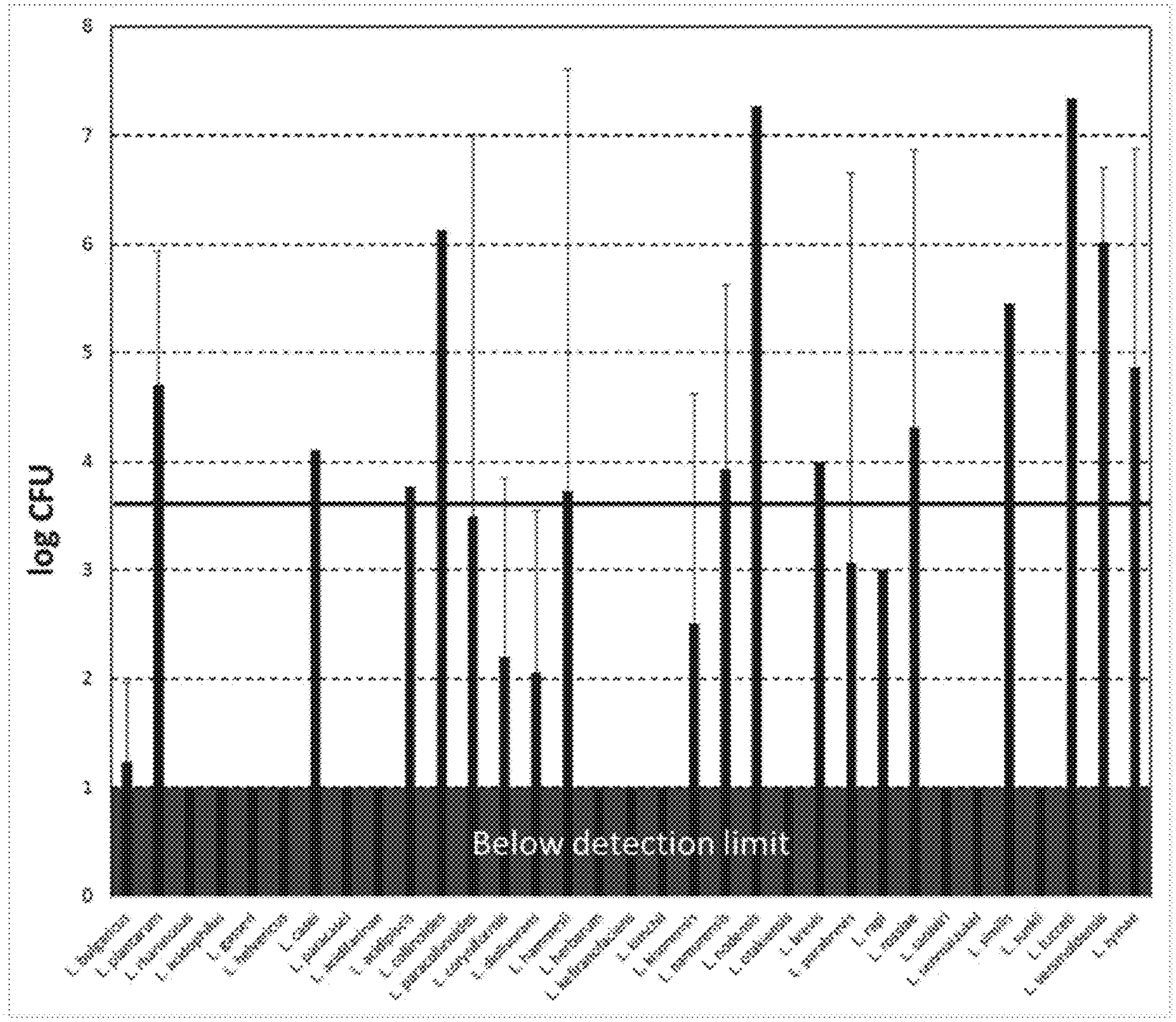
FIG. 1 is a graph showing the viability (in log cfu) of 80 strains (representing 33 *Lactobacillus* species) in a test yoghurt after storage for 30 days at 37° C. by assay A.

The inventors have surprisingly identified strains of the *Lactobacillus* genus, which can be added to a food product, such that both the viability of these strains in the food product and the pH of this food product are acceptably decreased, when stored at ambient temperature. Thus, this food product contains a high level of bacteria and has an acceptable pH, when stored at ambient temperature, for at least 6 months.

The invention is directed to a process for manufacturing a food product stable at ambient temperature, said process comprising:

1) providing an initial food product with a pH of between 3.4 and 4.6, in particular an initial low bacteria-containing food product with a pH of between 3.4 and 4.6 containing a level of bacteria which is no more than $1\times10^2$ CFU per g of said initial low bacteria-containing food product;

2) adding to the initial food product, in particular to the initial low bacteria-containing food product, one or more stable lactic acid bacteria in a total amount of at least $1.0\times10^5$ CFU per g, to obtain a food product stable at ambient temperature, characterized in that:

(i) each of said one or more stable lactic acid bacterium is selected from the group consisting of strains of species *Lactobacillus plantarum, Lactobacillus zymae, Lactobacillus rossiae, Lactobacillus collinoides, Lactobacillus similis, Lactobacillus versmoldensis, Lactobacillus acidipiscis, Lactobacillus hammesii, Lactobacillus namurensis, Lactobacillus nodensis* and *Lactobacillus tucceti*; and (ii) each of said one or more stable lactic acid bacterium, when added in an amount of $1\times10^7$ CFU per g to a test yogurt having a pH of 4.3, previously heat-treated at 75° C. for 25 seconds:

a) retains viability in an amount of at least $5.0\times10^3$ CFU/g after storing said test yoghurt 30 days at a temperature of 37° C.; and b) decreases the pH of said test yoghurt of at most 0.6 units after storing said test yoghurt 30 days at a temperature of 37° C.

The invention also relates to the use of one or more stable lactic acid bacteria for inoculation in an initial food product, in particular an initial low bacteria-containing food product, with a pH of between 3.4 and 4.6, wherein (i) said stable lactic acid bacterium is selected from the group consisting of strains of species *Lactobacillus plantarum, Lactobacillus zymae, Lactobacillus rossiae, Lactobacillus collinoides, Lactobacillus similis, Lactobacillus versmoldensis, Lactobacillus acidipiscis, Lactobacillus hammesii, Lactobacillus namurensis, Lactobacillus nodensis* and *Lactobacillus tucceti*; and (ii) said stable lactic acid bacterium, when added in an amount of $1\times10^6$ CFU per g to a test yogurt having a pH of 4.3, previously heat-treated at 75° C. for 25 seconds:

a) retains viability in an amount of at least $5.0\times10^3$ CFU/g after storing said test yoghurt 30 days at a temperature of 37° C.; and b) decreases the pH of said test yoghurt of at most 0.6 units after storing said test yoghurt 30 days at a temperature of 37° C.

Initial Food Product

An initial food product with a pH of between 3.4 and 4.6 is provided in step 1) of the process of the invention or provided in the use of the invention By "food product", it is meant any product which is intended for human consumption. According to the invention (and in particular step 2 of the process), the initial food product must be suitable for being inoculated with the one or more stable lactic acid bacteria. By "initial food product", it is meant a food product before addition of the one or more stable lactic acid bacteria, and therefore which does not contain stable lactic acid bacteria as defined herein. The initial food product must be distinguished from the "food product stable at ambient temperature" which contains stable lactic acid bacteria as defined herein.

In an embodiment, said initial food product is a fermented food product. Fermentation is carried out through the action of a bacteria starter by conversion of carbohydrates into acid. A "bacteria starter" is defined as a composition comprising or consisting of one or more bacteria which is able to start and perform the fermentation of a substrate. In a particular embodiment, said initial food product is an acetic acid-fermented food product, meaning that the fermentation is carried out through the action of acetic acid bacteria starter by conversion of carbohydrates into acetic acid. In an embodiment, said initial food product is a lactic acid-fermented food product, meaning that the fermentation is carried out through the action of lactic acid bacteria starter by conversion of carbohydrates into lactic acid. The expression "lactic acid bacteria" (LAB) relates to food-grade bacteria producing lactic acid as the major metabolic end-product of carbohydrate fermentation. Lactic acid bacteria are well known in the art, and include strains of the *Lactococcus* genus, of the *Streptococcus* genus, of the *Lactobacillus* genus, of the *Bifidobacterium* genus, of the *Leuconostoc* genus, of the *Enterococcus* genus, of the *Pediococcus* genus, of the *Brevibacterium* genus and of the *Propinibacterium* genus.

In an embodiment, said initial food product of step 1) is selected from the group consisting of a milk-based product, a fruit-based product such as fruit-based beverage, a vegetable-based product such as a vegetable-based beverage, a cereal-based product such as a cereal-based beverage, a rice-based product such as rice-based beverage, a nut-based product such as nut-based beverage, a soy-based product and any mixture thereof. By "milk-based product", "fruit-based product or beverage", "vegetable-based product or beverage", "cereal-based product or beverage", "rice-based product or beverage", "nut-based product or beverage" and "soy-based product", it is meant that the main component of the initial food product is respectively milk, fruit, vegetable, cereal, rice, nut and soy. In an embodiment, milk, fruit, vegetable, cereal, rice, nut and soy are the only component used as substrate to manufacture the milk-based product, fruit-based product or beverage, vegetable-based product or beverage, cereal-based product or beverage, rice-based product or beverage, nut-based product or beverage and soy-based product (as initial food products) respectively. The term "beverage" is defined in this application as a liquid food product.

In an embodiment, the milk-based product (as initial food product) is a fermented dairy product or a chemically-acidified dairy product. In an embodiment, a fermented dairy product, is selected from the group consisting of a fermented milk, a yoghurt, a cheese, sour cream, buttermilk and fermented whey. Fermented dairy products are well known in the art and are manufactured through the action of a lactic acid bacteria starter (as defined herein) on a milk substrate (the pH of milk substrate is around 6.5 to 7). A "milk substrate" is defined herein as any milk of mammal origin, including but not limited to, cow, sheep and goat milk. The milk may be in the native state, a reconstituted milk or a skimmed milk. The milk substrate, in particular the milk, is typically previously treated, in particular by standardization, addition of additives [e.g., sugar, sweeteners and/or stabilisers], homogenization and/or heat-treatment [e.g., pasteurization]. In a particular embodiment, the fermented milk is obtained by fermentation of milk with a lactic acid bacteria starter selected from the group consisting of a starter comprising a *Streptococcus thermophilus* strain, a starter comprising a strain from the *Lactobacillus* genus and a starter comprising a *Lactococcus lactis* strain. In a particular embodiment, said fermented milk is obtained by fermentation of milk with a lactic acid bacteria starter selected from the group consisting of a starter comprising or consisting of *Streptococcus thermophilus* and *Lactobacillus bulgaricus*, a starter comprising or consisting of *Streptococcus thermophilus* and *Lactobacillus johnsonii* and a starter comprising or consisting of *Streptococcus thermophilus* and *Lactobacillus fermentum*. In a particular embodiment, said fermented milk is a yoghurt.

In an embodiment, the fruit-based product (as initial food product) is a fruit-based beverage. In a particular embodiment, the fruit-based product is a fruit juice or a fermented fruit juice.

In an embodiment, the vegetable-based product (as initial food product) is a vegetable-based beverage. In a particular embodiment, the vegetable-based product is a vegetable juice or a fermented vegetable juice.

In an embodiment, the cereal-based product (as initial food product) is a cereal-based beverage. In a particular embodiment, the cereal-based product is a chemically-acidified cereal product, a fermented cereal product, a chemically-acidified cereal beverage or a fermented cereal beverage.

In an embodiment, the rice-based product (as initial food product) is a rice-based beverage. In a particular embodiment, the rice-based product is a chemically-acidified rice product, a fermented rice product, a chemically-acidified rice beverage or a fermented rice beverage.

In an embodiment, the nut-based product is a nut-based beverage. In a particular embodiment, the nut-based product is a chemically-acidified nut product, a fermented nut product, a chemically-acidified nut beverage or a fermented nut beverage. In a particular embodiment of any nut-based product described herein, the food product is a walnut-based product.

In an embodiment, the soy-based product (as initial food product) is a soy-based beverage. In a particular embodiment, the soy-based product is a fermented soy milk product.

In an embodiment, the term "initial food product" also cover any mixture of milk-based product, fruit-based product or beverage, vegetable-based product or beverage, cereal-based product or beverage, rice-based product or beverage, nut-based product or beverage and soy-based product as defined herein, such as, for example but not limited to, a mixture of a milk-based product and cereal-based beverage, or a mixture of a milk-based product and fruit-based beverage.

In an embodiment, said initial food product is an initial "low bacteria-containing" food product with a pH of between 3.4 and 4.6, i.e. is an initial food product as defined herein with a level of bacteria which is no more than $1\times10^2$ CFU per g of said initial low bacteria-containing food product. By "level of bacteria" used herein, it is meant the total amount of bacteria as calculated as cfu/g of product. The cfu count can be measured by plating dilution(s) of the product to be tested on MRS/M17/PCA agar [Atlas, 2010 Handbook of Microbiological Media, Fourth Edition, pages 986, 1231 and 1402].

Any initial low bacteria-containing food product can be used in step 1) of the process of the invention or in the use of the invention. According to the invention (and in particular step 2 of the process), the initial low bacteria-containing food product must be suitable for being inoculated with the stable bacteria.

In an embodiment, the initial food product naturally has a level of bacteria which is no more than $1\times10^2$ CFU per g of food product.

In another embodiment, the initial food product has a level of bacteria, other than the stable lactic acid bacteria as defined herein, which is more than $1\times10^2$ CFU per g of food product. The presence of bacteria, in particular lactic acid bacteria, can result from the use of these microorganisms (in particular as starter) during the manufacture of the initial food product, for example when the initial food product results from fermentation of a substrate (as explained above).

In an optional embodiment of the invention, the initial food product is therefore treated, previously to the inoculation of the stable LAB, so as to obtain an initial low bacteria-containing food product. By "treating", it is meant any treatment which inactivates the bacteria contained in the initial food product (e.g. which inhibits or reduces the bacteria growth or kills bacteria), so as to reduce the level of bacteria to no more than $1\times10^2$ CFU per g of the low bacteria-containing food product. Treatment means are well known in the art. In an embodiment, the initial food product is treated using means selected from the group consisting of high-pressure sterilization, irradiation, ultra-filtration and heat-treating. In a particular embodiment, the initial food product is heat-treated so as to reduce the level of bacteria to no more than $1\times10^2$ CFU per g of the low bacteria-containing food product.

By "heat-treating", it is meant any treatment based on temperature which inactivates the bacteria contained in the initial food product (e.g. which inhibits or reduces the bacteria growth or kills bacteria), so as to reduce the level of bacteria in the low bacteria-containing food product to no more than $1\times10^2$ CFU per g of the low bacteria-containing food product.

Thus, in an embodiment, the invention is directed to a process for manufacturing a food product stable at ambient temperature, said process comprising:

1) providing an initial food product with a pH of between 3.4 and 4.6;

1b) treating the initial food product so as to obtain a level of bacteria which is no more than $1\times10^2$ CFU per g [of the resulting initial low bacteria-containing food product], in particular by heat-treating said initial food product; and 2) adding to the initial low bacteria-containing food product, one or more stable lactic acid bacteria in a total amount of at least $1.0\times10^5$ CFU per g, to obtain a food product stable at ambient temperature, characterized in that:

(i) each of said one or more stable lactic acid bacterium is selected from the group consisting of strains of species *Lactobacillus plantarum, Lactobacillus zymae, Lactobacillus rossiae, Lactobacillus collinoides, Lactobacillus similis, Lactobacillus versmoldensis, Lactobacillus acidipiscis, Lactobacillus hammesii, Lactobacillus namurensis, Lactobacillus nodensis* and *Lactobacillus tucceti*; and (ii) each of said one or more stable lactic acid bacterium, when added in an amount of $1\times10^7$ CFU per g to a test yogurt having a pH of 4.3, previously heat-treated at 75° C. for 25 seconds:

a) retains viability in an amount of at least $5.0\times10^3$ CFU/g after storing said test yoghurt 30 days at a temperature of 37° C.; and b) decreases the pH of said test yoghurt of at most 0.6 units after storing said test yoghurt 30 days at a temperature of 37° C.

In an embodiment, the process of the invention is carried out in a fermented milk as defined herein, in particular a yoghurt as defined herein. Thus, the invention is directed to a process for manufacturing a fermented milk, in particular a yoghurt, stable at ambient temperature, said process comprising 1a) producing an initial fermented milk, in particular an initial yoghurt, with a pH of between 3.4 and 4.6 by fermentation of a milk substrate;

1b) treating, in particular heat-treating, said initial fermented milk, in particular said initial yoghurt, so as to obtain an initial low bacteria-containing fermented milk, in particular an initial low bacteria-containing yoghurt containing a level of bacteria which is no more than $1\times10^2$ CFU per g; and 2) adding to the initial low bacteria-containing fermented milk, in particular to the initial low bacteria-containing yoghurt, one or more of stable lactic acid bacteria strains in a total amount of at least $1.0\times10^5$ CFU per g to obtain a fermented milk, in particular a yoghurt, stable at ambient temperature, characterized in that:

(i) each of one or more said stable lactic acid bacterium is selected from the group consisting of strains of species *Lactobacillus plantarum, Lactobacillus zymae, Lactobacillus rossiae, Lactobacillus collinoides, Lactobacillus similis, Lactobacillus versmoldensis, Lactobacillus acidipiscis, Lactobacillus hammesii, Lactobacillus namurensis, Lactobacillus nodensis* and *Lactobacillus tucceti*; and (ii) each of one or more said stable lactic acid bacterium, when added in an amount of $1\times10^7$ CFU per g to a test yogurt having a pH of 4.3, previously heat-treated at 75° C. for 25 seconds:

a) retains viability in an amount of at least $5.0\times10^3$ CFU/g after storing said test yoghurt 30 days at a temperature of 37° C.; and b) decreases the pH of said test yoghurt of at most 0.6 units after storing said test yoghurt 30 days at a temperature of 37° C.

The initial, optionally low bacteria-containing, food product [in particular provided as such (step 1) or after treatment (step 1b) or after production by fermentation and treatment (step 1b)] must be suitable to reach the goal of the invention, i.e., to manufacture a food product stable at ambient temperature.

In an embodiment, the pH of the initial, optionally low bacteria-containing, food product is between 3.4 and 4.6. In an embodiment, the pH of the initial, optionally low bacteria-containing, food product is between 3.4 and 4.0. In an embodiment, the pH of the initial, optionally low bacteria-containing, food product is between 4.0 and 4.6. In an embodiment, the pH of the initial, optionally low bacteria-containing, food product is between 3.6 and 4.2. The pH can be determined by using any pH meter.

In an embodiment, optionally in combination with any embodiment of the previous paragraph, the sugar content of said initial, optionally low bacteria-containing, food product is between 0 and 13%. By "sugar content", it is meant the total content of sugar in the initial, optionally low bacteria-containing, food product, whether it is the sugar originally contained in the initial food product, sugar added into the initial food product or a combination of the sugar originally contained in the initial food product and sugar added into the initial food product. In an embodiment, the sugar content of said initial, optionally low bacteria-containing, food product is between 4 and 10%. In an embodiment, the sugar content of said initial, optionally low bacteria-containing, food product is between 6 and 9%. In a particular content, the sucrose content of said initial, optionally low bacteria-containing, food product is between 0 and 8%. In an embodiment, the sucrose content of said initial, optionally low bacteria-containing, food product is between 5 and 8%.

Adding/Inoculating One or More Stable Lactic Acid Bacteria to the Initial Food Product The initial food product as defined herein, in particular to the initial low bacteria-containing food product as defined herein, is inoculated with one or more stable lactic acid bacteria in a total amount of at least $1.0\times10^5$ CFU per g (step 2 of the process of the invention or use of the invention).

Within the context of the invention, "adding" is used interchangeably with "inoculating" (as well as "added" and "inoculated") and means that the one or more stable lactic acid bacteria (as defined herein) are put in contact with the initial food product. By "one or more", it is meant at least one lactic acid bacterium (LAB). In an embodiment, the number of LABs added to the food product is selected from the group consisting of 1, 2, 3, 4, 5, 6, 7, 8, 9 and 10. In an embodiment, 1 stable LAB is added to the food product. In an embodiment, 2 stable LABs are added to the food product. In an embodiment, 3 stable LABs are added to the food product. In an embodiment, 4 stable LABs are added to the food product. In an embodiment, 5 stable LABs are added to the food product.

The one or more stable LABs are added to the initial food product, in particular to the initial low bacteria-containing food product, in a total amount of at least $1\times10^5$ cfu per g of food product. When several (i.e., at least 2) stable LABs are added, "total amount" means the sum of each individual amount of inoculated stable LAB (as an example, addition of a first stable LAB at $3\times10^5$ cfu/g and of a second stable LAB at $7\times10^5$ cfu/g leads to a total amount of $1\times10^6$ cfu/g). In an embodiment, the one or more stable LABs are added to the initial food product, in particular to the initial low bacteria-containing food product, in a total amount selected from the group consisting of at least $5\times10^5$ CFU per g, at least $1\times10^6$ CFU per g, at least $5\times10^6$ CFU per g or at least $1\times10^7$ CFU per g of the initial food product. In an embodiment, the one or more stable LABs are added to the initial food product, in particular to the initial low bacteria-containing food product, in a total amount range selected from the group consisting of from $1\times10^5$ to $1\times10^8$ cfu per g, from $1\times10^6$ to $1\times10^8$ cfu per g and from $5\times10^6$ to $1\times10^8$ cfu per g.

The one or more stable LABs can be inoculated into the initial food product under any form, such as under frozen, dried, freeze-dried, liquid or solid format, in the form of pellets or frozen pellets, or in the form of a powder or dried powder. In an embodiment, the one or more stable LABs are added to the initial food product, under liquid form, for example as bulk starter [i.e., a LAB culture previously propagated in a growth medium to obtain the required concentration of inoculation]. In an embodiment, the one or more stable LABs are directly added to the initial food product under the form of concentrates, for example frozen or dried concentrates. In an embodiment the one or more stable LABs are added to the food product under liquid form as a dilution [e.g. in water or saline solution] of concentrates, such as of frozen or dried concentrates. The expression "directly inoculated" means that the one or more stable LABs are added into the initial food product without previous propagation. The direct inoculation requires that the concentration of the one or more stable LABs be high enough. Thus, the concentration of stable LABs in the frozen or dried concentrate is in the range of $10^8$ to $10^{12}$ cfu per g of concentrate, and more preferably at least $10^8$, at least $10^9$, at least $10^{10}$, at least $10^{11}$ or at least $10^{12}$ cfu/g of concentrate.

In an embodiment, said one or more strains are aseptically added to the initial food product. By "aseptically", it is meant that no other microorganisms than the one or more stable lactic acid bacteria are added to the food product, e.g. by using Tetra FlexDos™ aseptic in-line inoculation system.

The Stable Lactic Acid Bacteria (Stable LABs)

The one or more stable lactic acid bacteria (LABs) added to the initial food product (in step 2) of the claimed process of the invention or in the use of the invention) are characterized by the 2 following features:

(i) the one or more stable lactic acid bacteria strain is selected from the group consisting of strains of species *Lactobacillus plantarum, Lactobacillus zymae, Lactobacillus rossiae, Lactobacillus collinoides, Lactobacillus similis, Lactobacillus versmoldensis, Lactobacillus acidipiscis, Lactobacillus hammesii, Lactobacillus namurensis, Lactobacillus nodensis* and *Lactobacillus tucceti.*

In an embodiment, the one or more stable lactic acid bacteria strain is selected from the group consisting of strains of species *Lactobacillus plantarum, Lactobacillus zymae, Lactobacillus rossiae, Lactobacillus collinoides, Lactobacillus versmoldensis* and *Lactobacillus namurensis*. In an embodiment, the one or more stable lactic acid bacteria strain is selected from the group consisting of strains of species *Lactobacillus plantarum* and *Lactobacillus zymae.*

In an embodiment, the one or more stable lactic acid bacteria strain is of species *Lactobacillus plantarum*. In an embodiment, the one or more stable lactic acid bacteria strain is of species *Lactobacillus zymae*. In an embodiment, the one or more stable lactic acid bacteria strain is of species *Lactobacillus rossiae*. In an embodiment, the one or more stable lactic acid bacteria strain is of species *Lactobacillus collinoides*. In an embodiment, the one or more stable lactic acid bacteria strain is of species *Lactobacillus similis*. In an embodiment, the one or more stable lactic acid bacteria strain is of species *Lactobacillus versmoldensis*. In an embodiment, the one or more stable lactic acid bacteria strain is of species *Lactobacillus acidipiscis*. In an embodiment, the one or more stable lactic acid bacteria strain is of species *Lactobacillus hammesii*. In an embodiment, the one or more stable lactic acid bacteria strain is of species *Lactobacillus namurensis*. In an embodiment, the one or more stable lactic acid bacteria strain is of species *Lactobacillus nodensis*. In an embodiment, the one or more stable lactic acid bacteria strain is of species *Lactobacillus tucceti.*

For the avoidance of doubt, the *Lactobacillus* species described herein are as defined in the literature, in particular in Salvetti et al. 2012 Probiotics & Antimicro. Prot. 4 (4): 217-226, and Cay et al. 2012 Int. J. Syst. Evol. Microbiol. 62:1140-1144.

(ii) each of the one or more stable lactic acid bacteria strain remains viable in, and do not decrease significantly the pH of, a heat-treated yogurt stored 30 days at a temperature of 37° C. (i.e. under strict conditions).

Thus, in an embodiment, said stable lactic acid bacteria strain, when added in an amount of $1\times10^7$ CFU per g to a test yogurt having a pH of 4.3, previously heat-treated at 75° C. for 25 seconds:

a) retains viability in an amount of at least $5.0\times10^3$ CFU/g after storing said test yoghurt 30 days at a temperature of 37° C.; and
b) decreases the pH of said test yoghurt of at most 0.6 units after storing said test yoghurt 30 days at a temperature of 37° C.

In an embodiment, the sugar content of said test yogurt is between 0 and 13%. In an embodiment, the sugar content of said test yogurt is between 4 and 10%. In an embodiment, the sugar content of said test yogurt is between 6 and 9%. In a particular content, the sucrose content of said test yogurt is between 0 and 8%. In an embodiment, the sucrose content of said test yogurt is between 5 and 8%. In an embodiment, the sugar content of said test yogurt is between 12 and 13%, including a sucrose content between 7 and 9%.

In an embodiment, feature (ii) is tested applying assay A as described below:

- the inoculum of the LAB to be tested is prepared as follows: a culture of the LAB at $10^6$ cfu/ml is cultured in 10 mL MRS/M17 broth overnight at 37° C.; after 2 h at 4° C., the culture is centrifuged at 4000 rpm for 10 min; the pellet is resuspended in 10 mL sterile saline; the centrifugation/resuspension step is repeated a second time, to give the inoculum
- after standardization of the inoculum at around $1\times10^9$ CFU/mL, 0.4 mL of the inoculum was added into 40 mL of heat-treated yoghurt (2.8% protein, 3% fat, 12.5% of total sugar including 8% sucrose; pH 4.3) and well mixed [final stable LAB concentration in heat-treated yoghourt is around $1\times10^7$ CFU/g of yoghurt]; the tube is then sealed.
- the inoculated yoghurt is incubated at 37° C. for 30 days.
- after 30 days, the pH is determined by pH meter (Mettler Toledo, SevenEasy); the pH at day 30 is then compared to the pH of the heat-treated yoghurt at the time of LAB addition
- after 30 days, the CFU count is determined by plating on MRS/M17 agar as follows: 1 mL of yogurt sample was serial diluted by sterile saline to 10-7; MRS/M17 agar (1.5%) was melted and maintained at 48° C. in water bath; 1 mL of 10-1 to 10-7 dilution was added to petri dish and poured with 25 mL of the MRS/M17 agar; the plates were incubated at 37° C. anaerobically for 2 days for counting; the amount of LABs at day 30 is then compared to the amount of LAB added to the heat-treated yoghurt.

In an embodiment of the feature a), said stable lactic acid bacteria strain, when added in an amount of $1\times10^7$ CFU per g to a test yogurt having a pH of 4.3, previously heat-treated at 75° C. for 25 seconds (such as by applying assay A), retains viability in an amount of at least $5\times10^3$ CFU/g, at least $1\times10^4$ CFU/g, at least $5\times10^4$ CFU/g, at least $1\times10^5$ CFU/g, at least $5\times10^5$ CFU/g or at least $1\times10^6$ CFU/g, after storing said test yoghurt 30 days at a temperature of 37° C.

In an embodiment of the feature b), considered individually or in combination with the embodiment of the previous paragraph [feature a], said stable lactic acid bacteria strain, when added in an amount of $1\times10^7$ CFU per g to a test yogurt having a pH of 4.3, previously heat-treated at 75° C. for 25 seconds (such as by applying assay A), decreases the pH of said test yoghurt of at most 0.6 units, at most 0.5 units, at most 0.4 units or at most 0.3 units, after storing said test yoghurt 30 days at a temperature of 37° C.

In an embodiment, said stable lactic acid bacteria strain, when added in an amount of $1\times10^7$ CFU per g to a test yogurt having a pH of 4.3, previously heat-treated at 75° C. for 25 seconds (such as by applying assay A):

a) retains viability in an amount selected from the group consisting of at least $5.0\times10^3$ CFU/g, at least $1.0\times10^4$ CFU/g, at least $5.0\times10^4$ CFU/g, at least $1.0\times10^5$ CFU/g, at least $5.0\times10^5$ CFU/g or at least $1.0\times10^6$ CFU/g; and
b) decreases the pH of said test yoghurt of at most 0.6 units, at most 0.5 units, of at most 0.4 units or at most 0.3 units, after storing said test yoghurt 30 days at a temperature of 37° C.

In a particular embodiment, said stable lactic acid bacteria strain, when added in an amount of $1\times10^7$ CFU per g to a test yogurt having a pH of 4.3, previously heat-treated at 75° C. for 25 seconds (such as by applying assay A):

a) retains viability in an amount selected from the group consisting of at least $1\times10^4$ CFU/g, at least $5\times10^4$ CFU/g, at least $1\times10^5$ CFU/g, at least $5\times10^5$ CFU/g or at least $1\times10^6$ CFU/g; and b) decreases the pH of said test yoghurt of at most 0.6 units, at most 0.5 units, of at most 0.4 units or at most 0.3 units, after storing said test yoghurt 30 days at a temperature of 37° C.

In a particular embodiment, said stable lactic acid bacteria strain, when added in an amount of $1\times10^7$ CFU per g to a test yogurt having a pH of 4.3, previously heat-treated at 75° C. for 25 seconds (such as by applying assay A):

a) retains viability in an amount selected from the group consisting of at least $5\times10^3$ CFU/g or at least $1.0\times10^6$ CFU/g; and b) decreases the pH of said test yoghurt of at most 0.5 units, of at most 0.4 units or at most 0.3 units, after storing said test yoghurt 30 days at a temperature of 37° C.

In a particular embodiment, said stable lactic acid bacteria strain, when added in an amount of $1\times10^7$ CFU per g to a test yogurt having a pH of 4.3, previously heat-treated at 75° C. for 25 seconds (such as by applying assay A):

a) retains viability in an amount selected from the group consisting of at least $1\times10^4$ CFU/g, at least $5\times10^4$ CFU/g, at least $1\times10^5$ CFU/g, at least $5\times10^5$ CFU/g or at least $1\times10^6$ CFU/g; and b) decreases the pH of said test yoghurt of most 0.5 units, of at most 0.4 units or at most 0.3 units, after storing said test yoghurt 30 days at a temperature of 37° C.

In a particular embodiment, said stable lactic acid bacteria strain, when added in an amount of $1\times10^7$ CFU per g to a test yogurt having a pH of 4.3, previously heat-treated at 75° C. for 25 seconds (such as by applying assay A):

a) retains viability in an amount selected from the group consisting of at least $1\times10^5$ CFU/g, at least $5\times10^5$ CFU/g or at least $1\times10^6$ CFU/g; and b) decreases the pH of said test yoghurt of at most 0.3 units, after storing said test yoghurt 30 days at a temperature of 37° C.

Any *Lactobacillus plantarum, Lactobacillus zymae, Lactobacillus rossiae, Lactobacillus collinoides, Lactobacillus similis, Lactobacillus versmoldensis, Lactobacillus acidipiscis, Lactobacillus hammesii, Lactobacillus namurensis, Lactobacillus nodensis* and *Lactobacillus tucceti* strain fulfilling feature (ii) as defined herein, in particular when assessed by test A, can be used in the process of the invention or the use of the invention.

In an embodiment, said stable lactic acid bacteria strain is selected from the group consisting of strains of species *Lactobacillus plantarum, Lactobacillus zymae, Lactobacillus rossiae, Lactobacillus collinoides, Lactobacillus similis, Lactobacillus versmoldensis, Lactobacillus acidipiscis, Lactobacillus hammesii, Lactobacillus namurensis, Lactobacillus nodensis* and *Lactobacillus tucceti*, and, when added in an amount of $1\times10^7$ CFU per g to a test yogurt having a pH of 4.3, previously heat-treated at 75° C. for 25 seconds (such as by applying assay A):

a) retains viability in an amount selected from the group consisting of at least $5\times10^3$ CFU/g, at least $1\times10^4$ CFU/g, at least $5\times10^4$ CFU/g, at least $1\times10^5$ CFU/g, at least $5.0\times10^5$ CFU/g or at least $1\times10^6$ CFU/g; and b) decreases the pH of said test yoghurt of at most 0.6 units, at most 0.5 units, of at most 0.4 units or at most 0.3 units, after storing said test yoghurt 30 days at a temperature of 37° C.

In an embodiment, said stable lactic acid bacteria strain is selected from the group consisting of strains of species *Lactobacillus plantarum, Lactobacillus zymae, Lactobacillus rossiae, Lactobacillus collinoides, Lactobacillus versmoldensis, Lactobacillus hammesii, Lactobacillus similis, Lactobacillus nodensis, Lactobacillus tucceti* and *Lactobacillus namurensis*, and, when added in an amount of $1\times10^7$ CFU per g to a test yogurt having a pH of 4.3, previously heat-treated at 75° C. for 25 seconds (such as by applying assay A):

a) retains viability in an amount selected from the group consisting of at least $1\times10^4$ CFU/g, at least $5\times10^4$ CFU/g, at least $1\times10^5$ CFU/g, at least $5\times10^5$ CFU/g or at least $1\times10^6$ CFU/g; and b) decreases the pH of said test yoghurt of at most 0.6 units, at most 0.5 units, of at most 0.4 units or at most 0.3 units, after storing said test yoghurt 30 days at a temperature of 37° C.

In an embodiment, said stable lactic acid bacteria strain is selected from the group consisting of strains of species *Lactobacillus plantarum, Lactobacillus zymae, Lactobacillus rossiae, Lactobacillus collinoides, Lactobacillus versmoldensis, Lactobacillus similis* and *Lactobacillus namurensis*, and, when added in an amount of $1\times10^7$ CFU per g to a test yogurt having a pH of 4.3, previously heat-treated at 75° C. for 25 seconds (such as by applying assay A):

a) retains viability in an amount selected from the group consisting of at least $5\times10^3$ CFU/g, at least $1\times10^4$ CFU/g, at least $5\times10^4$ CFU/g, at least $1\times10^5$ CFU/g, at least $5\times10^5$ CFU/g or at least $1\times10^6$ CFU/g; and b) decreases the pH of said test yoghurt of at most 0.5 units, of at most 0.4 units or at most 0.3 units, after storing said test yoghurt 30 days at a temperature of 37° C.

In an embodiment, said stable lactic acid bacteria strain is selected from the group consisting of strains of species *Lactobacillus plantarum, Lactobacillus zymae, Lactobacillus rossiae, Lactobacillus collinoides, Lactobacillus versmoldensis, Lactobacillus similis* and *Lactobacillus namurensis*, and, when added in an amount of $1\times10^7$ CFU per g to a test yogurt having a pH of 4.3, previously heat-treated at 75° C. for 25 seconds (such as by applying assay A):

a) retains viability in an amount selected from the group consisting of at least $1\times10^4$ CFU/g, at least $5\times10^4$ CFU/g, at least $1\times10^5$ CFU/g, at least $5\times10^5$ CFU/g or at least $1\times10^6$ CFU/g; and b) decreases the pH of said test yoghurt of most 0.5 units, of at most 0.4 units or at most 0.3 units, after storing said test yoghurt 30 days at a temperature of 37° C.

In an embodiment, said stable lactic acid bacteria strain is selected from the group consisting of strains of species *Lactobacillus plantarum* and *Lactobacillus* zymae, and, when added in an amount of $1\times10^7$ CFU per g to a test yogurt having a pH of 4.3, previously heat-treated at 75° C. for 25 seconds (such as by applying assay A):

a) retains viability in an amount selected from the group consisting of at least $1\times10^5$ CFU/g, at least $5\times10^5$ CFU/g or at least $1\times10^6$ CFU/g; and b) decreases the pH of said test yoghurt of at most 0.3 units, after storing said test yoghurt 30 days at a temperature of 37° C.

In an embodiment, said stable lactic acid bacteria strain is of species *Lactobacillus plantarum*, and, when added in an amount of $1\times10^7$ CFU per g to a test yogurt having a pH of 4.3, previously heat-treated at 75° C. for 25 seconds (such as by applying assay A):

a) retains viability in an amount selected from the group consisting of at least $1\times10^5$ CFU/g, at least $5\times10^5$ CFU/g or at least $1\times10^6$ CFU/g; and b) decreases the pH of said test yoghurt of at most 0.3 units, after storing said test yoghurt 30 days at a temperature of 37° C.

In an embodiment, the one or more stable LABs, to be added to step 2) of the process of the invention or the be used in the use of the invention, is selected from the group consisting of the *Lactobacillus plantarum* strain DSM32493 deposited at the DSMZ on Apr. 26, 2017, a variant of the DSM32493 strain, the strain DSM33120 deposited at the DSMZ on May 22, 2019, a variant of the DSM33120 strain, the strain DSM33121 deposited at the DSMZ on May 22, 2019 and a variant of the DSM33121 strain.

In an embodiment, the one or more stable LABs, to be added to step 2) of the process of the invention or the be used in the use of the invention, is the *Lactobacillus plantarum* strain DSM32493 deposited at the DSMZ on Apr. 26, 2017, or a variant of the DSM32493 strain.

In an embodiment, the one or more stable lactic acid bacteria, to be added to step 2) of the process of the invention or to be used in the use of the invention, is a variant of the *Lactobacillus plantarum* strain DSM32493 deposited at the DSMZ on Apr. 26, 2017, wherein said variant bears a mutation (for example point mutation, deletion, insertion, . . . ) in the ATP synthase alpha subunit gene (as compared to the DSM32493 strain). The wild-type sequence of the ATP-synthase operon is as set forth in SEQ ID NO:1. The person skilled in the art knows how to determine whether this operon is mutated and how to measure the $H^+$-ATPase activity of a bacterium [see for example Jaichumjai et al. 2010; Food Microbiology 27 (2010) 741-748]. In an embodiment, the one or more stable lactic acid bacteria is a variant of DSM32493, wherein said variant has at least one mutation in the ATP synthase alpha subunit gene of the ATP-synthase operon (herein referred as "the ATP synthase alpha subunit gene"). In a particular embodiment, the one or more stable lactic acid bacteria is a variant of DSM32493, wherein the ATP synthase alpha subunit gene of said variant of DSM32493 as defined herein encodes a ATP synthase alpha subunit protein having an aspartic acid residue at position 169. In a particular embodiment, the one or more stable lactic acid bacteria is a variant of DSM32493, wherein said variant has at least one mutation in the ATP synthase alpha subunit gene of the ATP-synthase operon as defined in SEQ ID NO:2. In a particular embodiment, in combination with the previous embodiment on SEQ ID NO:2 or not, the one or more stable lactic acid bacteria is a variant of DSM32493 as defined herein, wherein said variant bears the mutation G to A at its position 506 of the ATP synthase alpha subunit gene (as compared to the DSM32493 strain). In a particular embodiment, the one or more stable lactic acid bacteria is a variant of DSM32493 as defined herein, wherein the ATP synthase alpha subunit gene of said variant is as defined in SEQ ID NO:4 (wherein the codon GGT at positions 505-507 is changed to GAT). In a particular embodiment, the one or more stable lactic acid bacteria, to be added to step 2) of the process of the invention, is a variant of DSM32493, wherein the ATP synthase alpha subunit gene of said variant of DSM32493 as defined herein encodes an ATP synthase alpha subunit protein as defined in SEQ ID NO:5.

In an embodiment, the one or more stable LABs, to be added to step 2) of the process of the invention or the be used in the use of the invention, is the *Lactobacillus plantarum* strain DSM33120 deposited at the DSMZ on May 22, 2019 or a variant of the DSM33120 strain.

In an embodiment, the one or more stable LABs, to be added to step 2) of the process of the invention or the be used in the use of the invention, is the *Lactobacillus plantarum* strain DSM33121 deposited at the DSMZ on May 22, 2019 or a variant of the DSM33121 strain.

*Lactobacillus plantarum* Strains

The invention is also directed to a *Lactobacillus plantarum* strain selected from the group consisting of the strain DSM33120 deposited at the DSMZ on May 22, 2019, a variant as defined herein of the DSM33120 strain, the strain DSM33121 deposited at the DSMZ on May 22, 2019 and a variant as defined herein of the DSM33121 strain.

In an embodiment, the invention is directed to a *Lactobacillus plantarum* strain selected from the group consisting of the strain DSM33120 deposited at the DSMZ on May 22, 2019 or a variant as defined herein of the DSM33120 strain. In an embodiment, the invention is directed to a *Lactobacillus plantarum* strain selected from the group consisting of the strain DSM33121 deposited at the DSMZ on May 22, 2019 or a variant as defined herein of the DSM33121 strain.

Bacterial Compositions

The invention is also directed to a bacterial composition comprising or consisting of a *Lactobacillus plantarum* strain selected from the group consisting of the strain DSM33120 deposited at the DSMZ on May 22, 2019, a variant as defined herein of the DSM33120 strain, the strain DSM33121 deposited at the DSMZ on May 22, 2019 and a variant as defined herein of the DSM33121 strain.

In a particular embodiment, the bacterial composition is a pure culture, i.e., comprises or consists of a single *Lactobacillus plantarum* strain of the invention. In another embodiment, the bacterial composition is a mixed culture, i.e., comprises or consists of a *Lactobacillus plantarum* strain of the invention and at least one other bacterium strain, in particular one other lactic acid bacterium.

In an embodiment, the bacterial composition, either as a pure or mixed culture as defined above, further comprises a food acceptable ingredient.

In a particular embodiment, the bacterial composition, either as a pure or mixed culture as defined above is under frozen, dried, freeze-dried, liquid or solid format, in the form of pellets or frozen pellets, or in a powder or dried powder. In a particular embodiment, the bacterial composition of the invention is in a frozen format or in the form of pellets or frozen pellets, in particular contained into one or more box or sachet. In another embodiment, the bacterial composition as defined herein is under a powder form, such as a dried or freeze-dried powder, in particular contained into one or more box or sachet.

In a particular embodiment, the bacterial composition of the invention, either as a pure culture or mixed culture as defined above, and whatever the format (frozen, dried, freeze-dried, liquid or solid format, in the form of pellets or frozen pellets, or in a powder or dried powder) comprises the *Lactobacillus plantarum* strain of the invention in a concentration comprised in the range of $10^5$ to $10^{12}$ cfu (colony forming units) per gram of the bacterial composition. In a particular embodiment, the concentration of the *Lactobacillus plantarum* strain within the bacterial composition of the invention is in the range of $10^7$ to $10^{12}$ cfu per gram of the bacterial composition, and in particular at least $10^7$, at least $10^8$, at least $10^9$, at least $10^{10}$ or at least $10^{11}$ CFU/g of the bacterial composition. In a particular embodiment, when in the form of frozen or dried concentrate, the concentration of the *Lactobacillus plantarum* strain of the invention—as pure culture or as a mixed culture—within the bacterial composition is in the range of $10^8$ to $10^{12}$ cfu/g of frozen concentrate or dried concentrate, and more preferably at least $10^8$, at least $10^9$, at least $10^{10}$, at least $10^{11}$ or at least $10^{12}$ cfu/g of frozen concentrate or dried concentrate.

Variants of *Lactobacillus plantarum* Strains

The features detailed herein for the variants of the deposited *Lactobacillus plantarum* strains apply to the *L. plantarum* strains added within the method of the invention, to the *L. plantarum* strains as such and the *L. plantarum* strains as part of the bacterial composition.

A variant of the DSM32493, DSM33120 or DSM33121 strain is herein defined as a *Lactobacillus plantarum* strain presenting at least one mutation, such as the addition, deletion, insertion and/or substitution of at least one nucleotide in its genome as compared to the DSM32493, DSM33120 or DSM33121 strain respectively. In a particular embodiment, the genome sequence of the variant has an identity of at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, at least 99.92%, at least 99.94%, at least 99.96%, at least 99.98%, or at least 99.99% to the genome sequence of the DSM32493, DSM33120 or DSM33121 strain respectively. Such a variant can be for example:

- a natural variant obtained spontaneously from the DSM32493, DSM33120 or DSM33121 strain after incubation in a selection medium. A natural variant is thus obtained without any genetic manipulation but only by spontaneous mutation of the strain and selection of the strain in an appropriate medium; an example of protocol used to select particular mutants of the DSM32493, DSM33120 or DSM33121 strain is disclosed in example 5; or
- a variant comprising at least one mutation in its genome, said mutation being induced by genetic engineering, for instance by directed mutagenesis or random mutagenesis. Random mutagenesis can be performed with UV radiations or mutagenic compounds such as nitrous acid, ethyl-methanesulfonate, NMethyl-N'-nitro-N-nitrosoguanidine, N-ethyl-N-nitrosourea, acridine orange, proflavine.

In an embodiment, said variant of the DSM32493, DSM33120 or DSM33121 strain (as defined herein), when added in an amount of $1\times10^7$ CFU per g to a test yogurt having a pH of 4.3, previously heat-treated at 75° C. for 25 seconds (such as by applying assay A):

a) retains viability in an amount selected from the group consisting of at least $5\times10^3$ CFU/g, at least $1\times10^4$ CFU/g, at least $5\times10^4$ CFU/g, at least $1\times10^5$ CFU/g, at least $5\times10^5$ CFU/g or at least $1\times10^6$ CFU/g; and b) decreases the pH of said test yoghurt of at most 0.6 units, at most 0.5 units, of at most 0.4 units or at most 0.3 units, after storing said test yoghurt 30 days at a temperature of 37° C.

In an embodiment, said variant of the DSM32493, DSM33120 or DSM33121 strain (as defined herein), when added in an amount of $1\times10^7$ CFU per g to a test yogurt having a pH of 4.3, previously heat-treated at 75° C. for 25 seconds (such as by applying assay A):

a) retains viability in an amount selected from the group consisting of at least $5\times10^3$ CFU/g or at least $1\times10^6$ CFU/g; and b) decreases the pH of said test yoghurt of at most 0.5 units, of at most 0.4 units or at most 0.3 units, after storing said test yoghurt 30 days at a temperature of 37° C.

In an embodiment, said variant of the DSM32493, DSM33120 or DSM33121 strain (as defined herein) keeps the at least same viability and the at most same pH decrease as the DSM32493, DSM33120 or DSM33121 strain respectively (when each added in an amount of $1\times10^7$ CFU per g to a test yogurt having a pH of 4.3, previously heat-treated at 75° C. for 25 seconds, such as by applying assay A), i.e. said variant of the DSM32493, DSM33120 or DSM33121 strain:

a) retains a viability identical to the viability retention of the DSM32493, DSM33120 or DSM33121 strain respectively or retains a higher viability than the viability retention of the DSM32493, DSM33120 or DSM33121 strain respectively (calculated in cfu/g); and b) decreases the pH of the test yoghurt identically to the pH decrease of the DSM32493, DSM33120 or DSM33121 strain respectively or decreases the pH less than the pH decrease of the DSM32493, DSM33120 or DSM33121 strain respectively (calculated in pH unit).

a Food Product Stable at Ambient Temperature

The aim of the process is to manufacture a food product stable at ambient temperature. The expression "stable at ambient temperature" when referring to a food product means a food product containing one or more stable lactic acid bacteria as defined herein, and for which both the amount of stable lactic acid bacteria and the pH is not significantly decreased when stored at ambient temperature.

Thus, a food product, as manufactured by the process of the invention, is considered stable when after storing this product for 180 days at a temperature of 25° C.:

- its pH is not decreased more than 0.7 unit; and
- the amount of stable lactic acid bacteria it contains is not decreased more than 3 log and/or is at least $1\times10^3$ CFU/g.

Thus, the food product is stored for 180 days at 25° C., from the day where the one or more stable lactic acid bacteria as defined herein are added to the initial food product (day 0). In an embodiment, the food product is stored under a sealed format (i.e., in closed sterile container).

After 180 days, the pH is determined by pH meter (Mettler Toledo, SevenEasy) and compared to the pH of the food product at day 0. Thus, in an embodiment, the pH of the food product at 180 days is not decreased more than 0.6 unit, more than 0.5 unit or more than 0.4 units (as compared to the pH at day 0).

After 180 days, the CFU count is determined as described in assay A detailed herein and compared with the amount of one or more stable lactic acid bacteria as defined herein added at day 0. Thus, in an embodiment, the amount of one or more stable lactic acid bacteria it contains is at least $1\times10^3$ CFU/g (as compared to the amount added at day 0), whatever the level of addition in step 2) (which is at least $1\times10^5$ CFU). In an embodiment, the amount of one or more stable lactic acid bacteria it contains is not decreased more than 3 log (as compared to amount added at day 0). In an embodiment, the amount of one or more stable lactic acid bacteria it contains is not decreased more than 2 log (as compared to amount added at day 0). In an embodiment, the amount of one or more stable lactic acid bacteria it contains is not decreased more than 3 log and is at least $1\times10^3$ CFU/g (as compared to the amount added at day 0). In an embodiment, the amount of one or more stable lactic acid bacteria it contains is not decreased more than 2 log and is at least $1\times10^3$ CFU/g (as compared to the amount added at day 0).

The invention also relates to a food product stable at ambient temperature, as defined herein or as obtained by the process of the invention, and containing one or more stable lactic acid bacteria as defined herein.

In an embodiment, the food product stable at ambient temperature, as defined herein or as obtained by the process of the invention, contains a *Lactobacillus plantarum* strain selected from the group consisting of the strain DSM33120 deposited at the DSMZ on May 22, 2019, a variant as defined herein of the DSM33120 strain, the strain DSM33121 deposited at the DSMZ on May 22, 2019 and a variant as defined herein of the DSM33121 strain.

In an embodiment, the food product stable at ambient temperature, as defined herein or as obtained by the process of the invention, contains a *Lactobacillus plantarum* strain selected from the group consisting of the strain DSM33120 deposited at the DSMZ on May 22, 2019 or a variant as defined herein of the DSM33120 strain. In an embodiment, the food product stable at ambient temperature, as defined herein or as obtained by the process of the invention, contains a *Lactobacillus plantarum* strain selected from the group consisting of the strain DSM33121 deposited at the DSMZ on May 22, 2019 or a variant as defined herein of the DSM33121 strain.

In an embodiment, the food product stable at ambient temperature of the invention (as such or as obtained by the process of the invention) has its pH which is not decreased more than 0.7 unit, and has the amount of stable lactic acid bacteria it contains not decreased more than 3 log and/or is at least $1\times10^3$ CFU/g, after storing this product for 180 days at a temperature of 25° C.

In an embodiment, the food product stable at ambient temperature of the invention (as such or as obtained by the process of the invention) is selected from the group consisting of a milk-based food product, a fruit-based food product such as fruit-based food beverage, a vegetable-based food product such as a vegetable-based food beverage, a cereal-based food product such as a cereal-based food beverage, a rice-based food product such as rice-based food beverage, a nut-based food product such as nut-based food beverage, a soy-based food product and any mixture thereof. In an embodiment, the milk-based food product food product stable at ambient temperature is a fermented dairy product or a chemically-acidified dairy product. In an embodiment, a fermented dairy product, is selected from the group consisting of a fermented milk, a yoghurt, a cheese, sour cream, buttermilk and fermented whey. In an embodiment, the milk-based food product is a fermented milk.

In an embodiment, the food product stable at ambient temperature of the invention—in particular the fermented dairy food product as defined herein—contains one or more said stable lactic acid bacterium selected from the group consisting of strains of species *Lactobacillus plantarum, Lactobacillus zymae, Lactobacillus rossiae, Lactobacillus collinoides, Lactobacillus similis, Lactobacillus versmoldensis, Lactobacillus acidipiscis, Lactobacillus hammesii, Lactobacillus namurensis, Lactobacillus nodensis* and *Lactobacillus tucceti*, wherein each of one or more said stable lactic acid bacterium, when added in an amount of $1\times10^7$ CFU per g to a test yogurt having a pH of 4.3, previously heat-treated at 75° C. for 25 seconds: a) retains viability in an amount of at least $5.0\times10^3$ CFU/g after storing said test yoghurt 30 days at a temperature of 37° C.; and b) decreases the pH of said test yoghurt of at most 0.6 units after storing said test yoghurt 30 days at a temperature of 37° C. In a particular embodiment, said one or more stable lactic acid bacteria strain are selected from the group consisting of strains of species *Lactobacillus plantarum, Lactobacillus zymae, Lactobacillus rossiae, Lactobacillus collinoides, Lactobacillus versmoldensis* and *Lactobacillus namurensis*. In a particular embodiment, said one or more stable lactic acid bacteria strain are selected from the group consisting of strains of species *Lactobacillus plantarum* and *Lactobacillus zymae*. In a particular embodiment, said one or more stable lactic acid bacteria strain are of the species *Lactobacillus plantarum*. In a particular embodiment, said one or more stable lactic acid bacteria strain is DSM32493 strain deposited at the DSMZ on Apr. 26, 2017 or any variant thereof as defined herein.

The definitions and specific embodiments detailed for the process of manufacture of the invention apply similarly in the context of the food product stable at ambient temperature of the invention, in particular for but not limited to, the lactic acid bacteria species, the number of lactic acid bacteria, the pH decrease feature after storing for 180 days at a temperature of 25° C. of the LAB to be added, the LAB viability retention feature after storing for 180 days at a temperature of 25° C. of the LAB to be added, any combination of this pH decrease and LAB viability retention features, the type of food product (such as beverage) and the nature of food product (such as milk-based, fruit-based, vegetable-based, cereal-based, rice-based, nut-based and soy-based food product and any mixture thereof).

Deposit and Expert Solution

The following deposits were made according to the Budapest treaty on the international recognition of the deposit of microorganisms for the purposes of patent procedure.

- *Lactobacillus plantarum* strain DGCC12411 deposited by DuPont Nutrition Biosciences ApS under accession number DSM32493 on Apr. 26, 2017, at the DSMZ [Deutsche Sammlung von Mikroorganismen und Zellkulturen GmbH, Inhoffenstrasse 7B, D-38124 Braunschweig-Germany];
- *Lactobacillus plantarum* strain DGCC12119 deposited by DuPont Nutrition Biosciences ApS under accession number DSM33120 on May 22, 2019, at the DSMZ; and
- *Lactobacillus plantarum* strain DGCC12480 deposited by DuPont Nutrition Biosciences ApS under accession number DSM33121 on May 22, 2019, at the DSMZ.

It is requested that the biological material shall be made available only by the issue of a sample to an expert nominated by the requester. In respect to those designations in which a European Patent is sought, a sample of the deposited microorganism will be made available until the publication of the mention of the grant of the European patent or until the date on which application has been refused or withdrawn or is deemed to be withdrawn, only by the issue of such a sample to an expert nominated by the person requesting the sample, and approved either i) by the Applicant and/or ii) by the European Patent Office, whichever applies (Rule 32 EPC).

SEQUENCES

SEQ ID NO: 1:
*L. plantarum* ATP-synthase operon
GTGGGTGATCCAGTTCCTACAGTCAAATTCCTTGGACTGACGTTTAATATCGCGAATGAC

ATCTCAGTAATTGTGACTTGTCTGATTGTTTTCTTGTTTGTTTTTTTACTTTCGCGACAT

TTAACAATGAAGCCCAAGGGTGGACAAAATGTGCTGGAGTGGCTCATCGAGTTCACGAAT

GGCATTGTCAAAGGGTCGATCAAGGGTAACGAAGCGTCTAACTTCGGTTTGTACGCATTT

ACATTGTTTCTCTTTATCTTCATCGCTAACCAACTTGGATTGTTCATTCACGTTCAGGTC

GGGCAGTATACGTATCTGAAGAGTCCAACCGCCGATCCGATTGTGACTTTGACGTTATCG

TTTATGACCGTTGCACTTGCACATGCTGCGGGTGTTCGTAAGAAAGGTATGGGTGGTTAT

TTGAAAGAATACACACAACCTTTTGCTGTTTTCTCGGTTGTTAACGTCTTTGAACAATTT

ACCGATTTCCTAACTTTAGGTCTTCGGCTGTTCGGGAACATCTTTGCTGGTGAAATGTTA

CTAACGAAGGTTGCTGATTTGGCAAAGAGCAACGGTTGGTTGAGCTATGTTTACTCATTT

CCAATTGAACTCTTATGGCAAGGTTTCTCAGTGTTTATCGGGAGCATTCAAGCGTTCGTG

TTCGTAACCTTGACTTCAGTTTATATTTCTCAGAAGGTTAACGACGAGGAATAATTTCTA

GTTTTTTAATTTTAAGGAGGATACACAGATTATGGGAGCAATTGCTGCAGGTATTGCTAT

GTGTGGTGCCGCTATAGGTGCTGGTATTGGTAACGGTTTGGTTATTTCTAAGATGCTTGA

AGGGATGGCCCGTCAACCAGAATTATCTGGTCAATTACGGACTAACATGTTCATCGGTGT

TGGGTTGGTCGAATCAATGCCTATAATTTCCTTCGTTGTTGCTTTGATGGTTATGAACAA

GTAATCATTGGTCAACGAGTTCATTTTAATGAAAATGAAAGAAGGAGGTGTCATTAGATG

CTCTCGCATTTAATTATCGGTGCATCCGGTCTCTACCTTGGTGATATGTTGTTTATCGGG

ATTAGCTTTATTGTTTTGATGGCATTGATCTCTGTTGTTGCTTGGAAGCCCATCACAAAA

ATGATGGCTGATCGAGCCGACAAGATTGCGAACGACATTGATTCAGCACAAAAGTCTCGG

CAAGAAGCGAGTGACTTAGCTGATCAACGGCGTGATGCGCTATCACACTCTCGCGCTGAA

GCGAGTGAAATTGTCGCTGACGCGAAAAAGAGTGGCGAAAAGCAACGGTCAAGTATCATT

GCCGATGCGCAAAACGAAGCAACGCAGTATAAACAAAATGCGCGTAAGGATATTGAACAG

GAGCGTCAAGATGCCTTGAAGAACGTCCAATCAGACGTCGCTGACATTTCGATTGCGATT

GCTACGAAGATTATTAAGAAGCAATTGGATCCGGAAGGCCAACAGGCATTAATTAATTCG

TATATTGAAGGGTTGGGAAAGCATGAGTCTTGATAATCTTACAATTGCAAGTCGTTATTC

AAAGGCACTCTTTGAACTTGCAGTTGAAAAAGATCAGACCGAAGCATTCCTGGCCGAGTT

AAAGCAATTACGGCAAGTCTTTGTCGACAACCCGCAATTGGCAGAGGTCCTCTCAGGATC

ATTGCTTCCGGTTGATCAAAAACAGACAACGTTGTCAACTTTGACTGACCACGCTTCAGA

ATACATTAAAAACTTTATTCAAATGTTGTATGATTACGGCCGCATGTCGAACTTAGTTGG

CATTGTTGACGCGTTTGAAGCACGTTTCGATGAGAGTCGCAAAATAGTGCATGCCGAAGT

AACGTCTGCGGTCAAGTTGTCAGATGAGCAAGCTGATGCAATCGCAAAGGCATTCGCCAA

ACGTGTTGGGGCCAATCAGGTTGTTTTGTCACGTAAAGTCGATGAAGCAATCATTGGCGG

TGTAATTGTGAAGTCAAATAATCAAACGTTTGATGGTAGCGTTGCGTTACAACTAACGAA

TTTAAGACGAGCACTCATCAACAATTAGTTTACGAAGAGGTGAAACTTTTATGAGCATTA

AATCTGAAGAAATCAGTGCTCTAATCAAACAACAATTAGAAAGTTATCAAACTGAGCTCT

CAGTTGCTGAAACCGGTACTGTCACCTACGTTGGTGATGGGATCGCCCGTGCTCACGGAC

TCGACAACGCCTTACAAGGTGAATTACTCGAATTCAGTAACGGAGTTTACGGGATGGTAC

-continued

AAAACCTCGAAAGCAACGATGTTGGTATCGTTGTTTTAGGGGATTTTGATGGTATTCGTG

AAGGCGATACTGTTAAGCGGACTGGCCGCATCATGGAAGTTCCAGTCGGTGACGCCATGA

TTGGCCGGGTCGTTAACCCATTAGGTCAACCAGTTGACGGTTCAGGTGAGATTAAGACCA

CGAATACGCGGCCAATCGAACATAAAGCTCCTGGTATTATGCAACGGCAATCAGTTAGCG

AACCACTTCAAACTGGGATCAAGGCCATTGATGCCTTAGTTCCAATTGGTCGGGGCCAAC

GTGAATTGATTATCGGTGACCGTAAGACTGGGAAGACGTCCGTTGCCATTGATGCCATTT

TGAACCAAAAGGACCAAGACATGATTTGTGTCTACGTTGCAATCGGTCAAAAGGACTCAA

CTGTACGGGCCCAAGTTGAAACGTTGAAGAAGTTAGGTGCGATGGACTACACAATCGTTG

TAACTGCCGGACCTGCTGAACCAGCGCCATTACTGTACTTAGCTCCTTATGCTGGGGCAG

CGATGGGTGAAGAATTTATGATGAACGGCAAGCACGTTTTGATCGTCTATGATGACCTTT

CAAAGCAAGCAACGGCTTACCGTGAACTTTCCTTGATCCTCCGTCGTCCTCCAGGTCGTG

AAGCTTATCCTGGGGATGTCTTCTACTTGCACTCACGGTTACTCGAACGGGCTGCCAAGT

TGAGCGATGAATTGGGTGGCGGTTCAATGACGGCCTTACCAATTATCGAAACGCAAGCTG

GGGATATTTCGGCTTATATTCCAACTAACGTTATTTCAATCACCGATGGGCAAATCTTCT

TGGATAGTGATTCATTCTATTCAGGTGTGCGGCCAGCGATTGATGCCGGGGCCTCTGTTT

CCCGGGTTGGTGGGGATGCGCAAATTAAAGCGATGAAGTCCGTTGCCGGGACCTTGCGTC

TTGACTTGGCTTCTTATCGTGAATTGGAATCCTTCTCACAATTCGGTTCTGACTTGGATG

CTGCAACCCAAGCGAAATTAAATCGTGGGCAACGGATCGTTGAAGTCTTAAAACAACCTG

TTCATTCACCATTGAAGGTCGAAGAACAAGTAATGATTTTATATGCTTTGACCAACGGTT

ATTTGGATAAAGTGGCAGTTGATGATATTGCCCGTTACCAAAGTGAATTGTTTGAATTTA

TTCATGCTAGTCATCAGGACCTCTTTGATACGATTTTGGCAACCAAGAAGTTACCAGAAG

CTGATAAGATGAATGGGGCCTTAGATGCGTTTGCAGAACAATTCCAGCCAACCGCTGCCG

CTGCGAAGTAGTTATGGCTGAAAAGGATGGTGAGTAGTGCATGGCAGAATCATTAATGGA

TGTCAAGCGCCGAATTGACTCAACAAAGAAGACTCATCAAATTACGTCGGCAATGCAAAT

GGTCTCAACTTCAAAATTGAACCAGATTCAAAAGCATACCAGCACGTATCAGGTGTACGC

TTCTAAAGTTGAAAGCATCGTTTCACATCTTGCCAAAGCTCATCTGATGTCAGCAAGTGC

CGGTGTTGCTAACAGTAATTCGAACACGATTTCAGTTAGTGAATTGCTCGCGCAACGCCC

CGTTAAAAAGACTGGTTTATTGGTGATCACTTCGGACCGTGGCCTCGTTGGTAGTTACAA

CAGTAACGTGTTGAAACAGACTAACGATTTCATGCGGACGCACAAGGTTGATGCCGATAA

CGCAGTCGTTTTGGCGGTTGGTGGCACTGGTGCGGATTTCTATAAAAAGAACGGGTTAAA

CGTGGCTTATGAGTACCGCGGCGTCTCTGATGTCCCAACTTTTAAAGAGGTTCGTGAAAT

CGTTAAGACAGTCACATCAATGTACCACAACGAAGTCTTTGATGAACTTTACGTCTTCTA

CAACCACTTTATTAATCGGCTCTCTTCTGGTTTTCGGGCCGTTAAGATGTTACCGATCTC

CGAAGAGACCTTTGAACAAAGTGAGTCAGATAATCGTAAAGCCAAGGATAGCCGGGTAGA

TGTCGGTCCCGAGTATGAAATGGAACCGTCAGAAGAAGCCATTTTGTCGGCCGTGTTGCC

ACAATATGCTGAAAGCTTGGTTTATGGTGCAATCTTGGATGCCAAGACTGCTGAACATGC

TTCGTCGTCAACCGCGATGAAGGCTGCATCAGATAACGCTGGCGATTTAATCGATAAATT

AAATCTGAAATATAACCGTGCGCGTCAAGCTGCTATTACCACTGAAATCACTGAAATCAC

TGGTGGTTTGGTTGCGCAAGAATAACGAAGTGGGAGGAATTAACGACTAATGAGTACAGG

TAAAGTTGTACAAGTTATTGGACCCGTTGTTGACGTTGAATTCTCTCTAAACGATAAGTT

ACCCGATATTAATAACGCCTTGATCATTCAGAAGGACAACGATGACACTTTAACGGTGGA

-continued

AGTATCGTTGGAATTAGGTGATGGGGTTGTTCGGACCGTCGCGATGGATGGTACGGATGG

CTTGCGCCGGGGAATGACAGTTGAAGACACTGGTTCTTCAATTACTGTTCCCGTTGGTAA

AGAGACGTTAGGCCGGGTCTTCAACGTTTTAGGGGAAACCATTGATGGTGGTCCAGAATT

CGGTCCAGACGCAGAACGTAACCCGATTCATCGGGATGCGCCTAAATATGATGAATTAAC

GACCAGTACTGAAGTATTGGAAACTGGAATTAAAGTTATTGACCTCTTAGCACCTTATGT

TCGTGGTGGTAAGATTGGGTTGTTCGGTGGTGCCGGTGTTGGTAAAACTGTTTTAATCCA

GGAATTAATTCATAACATTGCCCAAGAACATAACGGGATTTCCGTGTTTACCGGTGTTGG

TGAACGGACGCGTGAAGGGAATGACCTTTACTTCGAAATGAAGGCTTCCGGCGTTTTGAA

GAATACCGCCATGGTTTATGGTCAAATGAACGAACCACCTGGTGCCCGGATGCGGGTGGC

CTTGACCGGTTTGACGATTGCGGAATACTTCCGTGATGTTCAAGGTCAAGACGTGTTGTT

ATTCATCGACAATATCTTCCGGTTCACGCAAGCTGGTTCTGAAGTTTCCGCCTTACTTGG

TCGGATTCCTTCAGCCGTTGGTTACCAACCAACCTTAGCCACTGAAATGGGTCAATTACA

AGAACGGATCACTTCTACCAAGAAGGGGTCAGTTACTTCGATTCAAGCCGTTTATGTACC

TGCCGATGATTATACCGACCCGGCACCTGCAACGACTTTCGCCCATTTGGATGCGACGAC

CAACTTGGAACGTTCTTTGACGGAACAAGGGATCTACCCAGCCGTTGACCCATTAGCTTC

TTCTTCAATCGCTCTGGACCCATCAATCGTGGGCGAAGAACATTATCAAGTTGCAACGGA

AGTTCAACGGGTCTTGCAACGTTATCGTGAATTGCAAGATATTATCTCGATTTTAGGGAT

GGATGAATTATCTGACGAAGAAAAGACAACTGTTGCGCGTGCACGGCGGATTCAATTCTT

CTTGTCACAAAACTTCTTCGTTGCCGAAAACTTTACGGGCCAACCTGGTTCGTATGTGCC

AATCAACGATACCATCAAGGGCTTCAAAGAAATTCTTGAAGGTAAATATGATGACCTACC

AGAAGACGCATTCCGTCAAGTTGGTAAGATCGACGACGTGGTCGAAAAAGCGAAATCGAT

GGTAACTGATTAGGAGGGGTTTACATGGCTGACAATGCAAAATCATTAACCGTTAGCATC

GTAACTCCAGACGGTCAGGTCTATGAGAATAAGACGCCAATGTTGATCGTGCGAACGATT

GACGGCGAACTCGGAATTTTGCCGAACCATATTCCTGTGATTGCATCGCTTGCAATCGAT

GAGGTTCGGATCAAGCAACTTGAAAGTGATCAGGAAGATGACGAAATTGCCGTTAATGGT

GGTTTTGTTGAGTTCAGTAATAATACGGCAACGATTGTTGCCGATAGTGCTGAACGTCAG

AATGACATTGACGTTGCTCGAGCTGAAAATGCACGGAAACGCGCTGAAACACGGATTCAA

AATGCCCAACAAAAGCACGATGATGCTGAGTTGGCGCGGGCCCAAGTCGCTTTGCGGCGT

GCCATGAACCGTTTGAATGTTGCTCGGCATTAA

SEQ ID NO: 2:
ATP synthase alpha subunit gene of the DSM32493 strain
ATGAGCATTAAATCTGAAGAAATCAGTGCTCTAATCAAACAACAATTAGAAAGTTATCAA

ACTGAGCTCTCAGTTGCTGAAACCGGTACTGTCACCTACGTTGGTGATGGGATCGCCCGT

GCTCACGGACTCGACAACGCCTTACAAGGTGAATTACTCGAATTCAGTAACGGAGTTTAC

GGGATGGTACAAAACCTCGAAAGCAACGATGTTGGTATCGTTGTTTTAGGGGATTTTGAT

GGTATTCGTGAAGGCGATACTGTTAAGCGGACTGGCCGCATCATGGAAGTTCCAGTCGGT

GACGCCATGATTGGCCGGGTCGTTAACCCATTAGGTCAACCAGTTGACGGTTCAGGTGAG

ATTAAGACCACGAATACGCGGCCAATCGAACATAAAGCTCCTGGTATTATGCAACGGCAA

TCAGTTAGCGAACCACTTCAAACTGGGATCAAGGCCATTGATGCCTTAGTTCCAATTGGT

CGGGGCCAACGTGAATTGATTATCGGTGACCGTAAGACTGGGAAGACGTCCGTTGCCATT

-continued

GATGCCATTTTGAACCAAAAGGACCAAGACATGATTTGTGTCTACGTTGCAATCGGTCAA

AAGGACTCAACTGTACGGGCCCAAGTTGAAACGTTGAAGAAGTTAGGTGCGATGGACTAC

ACAATCGTTGTAACTGCCGGACCTGCTGAACCAGCGCCATTACTGTACTTAGCTCCTTAT

GCTGGGGCAGCGATGGGTGAAGAATTTATGATGAACGGCAAGCACGTTTTGATCGTCTAT

GATGACCTTTCAAAGCAAGCAACGGCTTACCGTGAACTTTCCTTGATCCTCCGTCGTCCT

CCAGGTCGTGAAGCTTATCCTGGGGATGTCTTCTACTTGCACTCACGGTTACTCGAACGG

GCTGCCAAGTTGAGCGATGAATTGGGTGGCGGTTCAATGACGGCCTTACCAATTATCGAA

ACGCAAGCTGGGGATATTTCGGCTTATATTCCAACTAACGTTATTTCAATCACCGATGGG

CAAATCTTCTTGGATAGTGATTCATTCTATTCAGGTGTGCGGCCAGCGATTGATGCCGGG

GCCTCTGTTTCCCGGGTTGGTGGGGATGCGCAAATTAAAGCGATGAAGTCCGTTGCCGGG

ACCTTGCGTCTTGACTTGGCTTCTTATCGTGAATTGGAATCCTTCTCACAATTCGGTTCT

GACTTGGATGCTGCAACCCAAGCGAAATTAAATCGTGGGCAACGGATCGTTGAAGTCTTA

AAACAACCTGTTCATTCACCATTGAAGGTCGAAGAACAAGTAATGATTTTATATGCTTTG

ACCAACGGTTATTTGGATAAAGTGGCAGTTGATGATATTGCCCGTTACCAAAGTGAATTG

TTTGAATTTATTCATGCTAGTCATCAGGACCTCTTTGATACGATTTTGGCAACCAAGAAG

TTACCAGAAGCTGATAAGATGAATGGGGCCTTAGATGCGTTTGCAGAACAATTCCAGCCA

ACCGCTGCCGCTGCGAAGTAG

SEQ ID NO: 3:
ATP synthase alpha subunit protein of the DSM32493 strain
MSIKSEEISALIKQQLESYQTELSVAETGTVTYVGDGIARAHGLDNALQGELLEFSNGVY

GMVQNLESNDVGIVVLGDFDGIREGDTVKRTGRIMEVPVGDAMIGRVVNPLGQPVDGSGE

IKTTNTRPIEHKAPGIMQRQSVSEPLQTGIKAIDALVPIGRGQRELIIGDRKTGKTSVAI

DAILNQKDQDMICVYVAIGQKDSTVRAQVETLKKLGAMDYTIVVTAGPAEPAPLLYLAPY

AGAAMGEEFMMNGKHVLIVYDDLSKQATAYRELSLILRRPPGREAYPGDVFYLHSRLLER

AAKLSDELGGGSMTALPIIETQAGDISAYIPTNVISITDGQIFLDSDSFYSGVRPAIDAG

ASVSRVGGDAQIKAMKSVAGTLRLDLASYRELESFSQFGSDLDAATQAKLNRGQRIVEVL

KQPVHSPLKVEEQVMILYALINGYLDKVAVDDIARYQSELFEFIHASHQDLFDTILATKK

LPEADKMNGALDAFAEQFQPTAAAAK

SEQ ID NO: 4:
ATP synthase alpha subunit gene of a variant of DSM32493 strain
ATGAGCATTAAATCTGAAGAAATCAGTGCTCTAATCAAACAACAATTAGAAAGTTATCAA

ACTGAGCTCTCAGTTGCTGAAACCGGTACTGTCACCTACGTTGGTGATGGGATCGCCCGT

GCTCACGGACTCGACAACGCCTTACAAGGTGAATTACTCGAATTCAGTAACGGAGTTTAC

GGGATGGTACAAAACCTCGAAAGCAACGATGTTGGTATCGTTGTTTTAGGGGATTTTGAT

GGTATTCGTGAAGGCGATACTGTTAAGCGGACTGGCCGCATCATGGAAGTTCCAGTCGGT

GACGCCATGATTGGCCGGGTCGTTAACCCATTAGGTCAACCAGTTGACGGTTCAGGTGAG

ATTAAGACCACGAATACGCGGCCAATCGAACATAAAGCTCCTGGTATTATGCAACGGCAA

TCAGTTAGCGAACCACTTCAAACTGGGATCAAGGCCATTGATGCCTTAGTTCCAATTGGT

CGGGGCCAACGTGAATTGATTATCGATGACCGTAAGACTGGGAAGACGTCCGTTGCCATT

GATGCCATTTTGAACCAAAAGGACCAAGACATGATTTGTGTCTACGTTGCAATCGGTCAA

AAGGACTCAACTGTACGGGCCCAAGTTGAAACGTTGAAGAAGTTAGGTGCGATGGACTAC

ACAATCGTTGTAACTGCCGGACCTGCTGAACCAGCGCCATTACTGTACTTAGCTCCTTAT

-continued

GCTGGGGCAGCGATGGGTGAAGAATTTATGATGAACGGCAAGCACGTTTTGATCGTCTAT

GATGACCTTTCAAAGCAAGCAACGGCTTACCGTGAACTTTCCTTGATCCTCCGTCGTCCT

CCAGGTCGTGAAGCTTATCCTGGGGATGTCTTCTACTTGCACTCACGGTTACTCGAACGG

GCTGCCAAGTTGAGCGATGAATTGGGTGGCGGTTCAATGACGGCCTTACCAATTATCGAA

ACGCAAGCTGGGGATATTTCGGCTTATATTCCAACTAACGTTATTTCAATCACCGATGGG

CAAATCTTCTTGGATAGTGATTCATTCTATTCAGGTGTGCGGCCAGCGATTGATGCCGGG

GCCTCTGTTTCCCGGGTTGGTGGGGATGCGCAAATTAAAGCGATGAAGTCCGTTGCCGGG

ACCTTGCGTCTTGACTTGGCTTCTTATCGTGAATTGGAATCCTTCTCACAATTCGGTTCT

GACTTGGATGCTGCAACCCAAGCGAAATTAAATCGTGGGCAACGGATCGTTGAAGTCTTA

AAACAACCTGTTCATTCACCATTGAAGGTCGAAGAACAAGTAATGATTTTATATGCTTTG

ACCAACGGTTATTTGGATAAAGTGGCAGTTGATGATATTGCCCGTTACCAAAGTGAATTG

TTTGAATTTATTCATGCTAGTCATCAGGACCTCTTTGATACGATTTTGGCAACCAAGAAG

TTACCAGAAGCTGATAAGATGAATGGGGCCTTAGATGCGTTTGCAGAACAATTCCAGCCA

ACCGCTGCCGCTGCGAAGTAG

SEQ ID NO: 5:
ATP synthase alpha subunit protein of a variant of DSM32493 strain
MSIKSEEISALIKQQLESYQTELSVAETGTVTYVGDGIARAHGLDNALQGELLEFSNGVY

GMVQNLESNDVGIVVLGDFDGIREGDTVKRTGRIMEVPVGDAMIGRVVNPLGQPVDGSGE

IKTTNTRPIEHKAPGIMQRQSVSEPLQTGIKAIDALVPIGRGQRELIIDDRKTGKTSVAI

DAILNQKDQDMICVYVAIGQKDSTVRAQVETLKKLGAMDYTIVVTAGPAEPAPLLYLAPY

AGAAMGEEFMMNGKHVLIVYDDLSKQATAYRELSLILRRPPGREAYPGDVFYLHSRLLER

AAKLSDELGGGSMTALPIIETQAGDISAYIPTNVISITDGQIFLDSDSFYSGVRPAIDAG

ASVSRVGGDAQIKAMKSVAGTLRLDLASYRELESFSQFGSDLDAATQAKLNRGQRIVEVL

KQPVHSPLKVEEQVMILYALTNGYLDKVAVDDIARYQSELFEFIHASHQDLEDTILATKK

LPEADKMNGALDAFAEQFQPTAAAAK

Various preferred features and embodiments of the present invention will now be described by way of non-limiting examples.

EXAMPLES

Example 1: Screening of Stable Lactic Acid Bacteria (Species)

Stable lactic acid bacteria were selected using assay A as described below:

Inoculum Preparation

Each LAB to be tested was prepared as follows: a culture of the LAB at $10^6$ cfu/ml was cultured in 10 mL MRS/M17 broth overnight at 37° C.; after 2 h at 4° C., the culture was centrifuged at 4000 rpm for 10 min; the pellet was resuspended in 10 mL sterile saline; the centrifugation/resuspension step was repeated a second time. The inoculum was standardized at an amount of around $1\times10^9$ CFU/ml. The *Lactobacillus* species listed in Table 1 were tested.

Test Yoghurt

A yoghurt having the following features—2.8% protein, 3% fat, 12.5% of total sugar including 8% sucrose; pH 4.3—was heat-treated to reduce the level of bacteria to less than $1\times10^2$ CFU per g.

Addition/Inoculation 0.4 mL of the prepared inoculum was added into 40 mL of the heat-treated yoghurt (in tube) and well mixed. The tube was then sealed. The concentration of stable LAB added into the heat-treated yoghurt (day 0) was around $1\times10^7$ CFU/g of yoghurt.

Storage

The sealed tube was then stored at 37° C. for 30 days. These conditions were considered to represent an accelerated model of storage at ambient temperature.

At day 30, the pH and the amount of stable LAB (cell count) were determined, and the difference with respectively the pH and amount of added stable LAB at day 0 was calculated.

pH and Cell Count Measurement

The pH was determined by pH meter (Mettler Toledo, SevenEasy)

The CFU count was determined by plating on MRS/M17 agar as follows: 1 mL of yogurt sample (day 30) was serial diluted by sterile saline to 10-7; MRS/M17 agar (1.5%) was melted and maintained at 48° C. in water bath; 1 mL of 10-1 to 10-7 dilution was added to petri dish and poured with 25 mL of the MRS/M17 agar; the plates were incubated at 37° C. anaerobically for 2 days for counting.

Selection

The two following features were considered for selecting stable LABs:

an amount of LAB of at least $5\times10^3$ cfu (3.69 log 10 cfu); and a pH decrease of at most 0.6 unit (i.e., a pH of at least 3.7).

Figure 2:
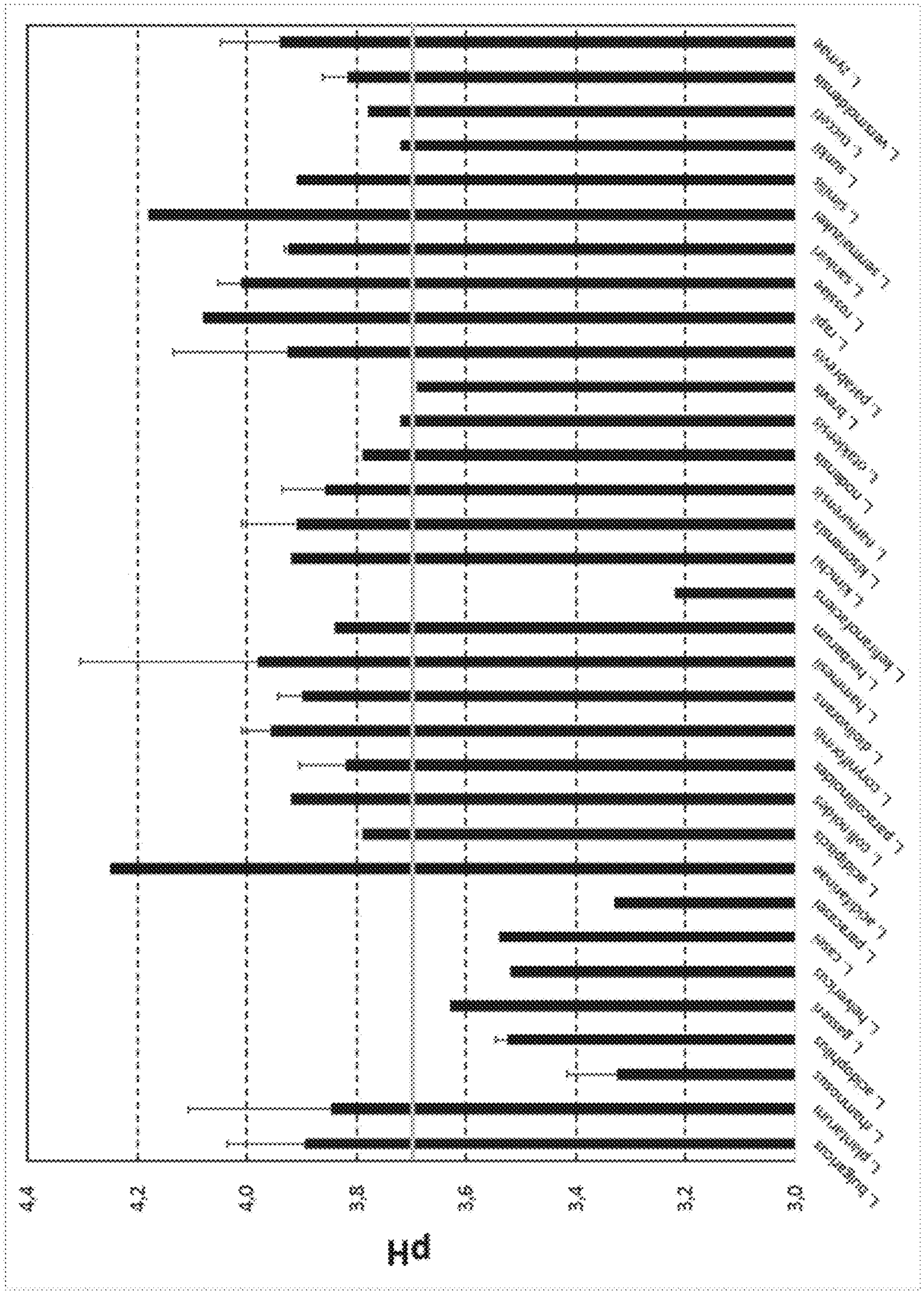
FIG. 2 is a graph showing the pH of a test yoghurt inoculated with one of 80 strains (33 *Lactobacillus* species) after storage for 30 days at 37° C. by assay A.

Results 80 strains, representative of 33 species, were tested and selected by assay A. The level of strains (cfu) in the yoghurt and the pH of the yoghurt, after storage at 37° C. for 30 days is summarized in Table 1, and represented in FIG. 1 (log cfu) and FIG. 2 (pH).

TABLE 1

| Species | # strain | Log cfu average | Log cfu STD | pH average | pH STD | selection |
|---|---|---|---|---|---|---|
| *L. bulgaricus* | 19 | 1.24 | 0.73 | 3.89 | 0.14 | no |
| *L. plantarum* | 4 | 4.71 | 1.23 | 3.85 | 0.26 | yes |
| *L. rhamnosus* | 2 | 1.00 | 0.00 | 3.33 | 0.09 | no |
| *L. acidophilus* | 2 | 1.00 | 0.00 | 3.53 | 0.02 | no |
| *L. gasseri* | 1 | 1.00 | n.a. | 3.63 | n.a. | no |
| *L. helvericus* | 1 | 1.00 | n.a. | 3.52 | n.a. | no |
| *L. casei* | 1 | 4.11 | n.a. | 3.54 | n.a. | no |
| *L. paracasei* | 1 | 1.00 | n.a. | 3.33 | n.a. | no |
| *L. acidifarinae* | 1 | 1.00 | n.a. | 4.25 | n.a. | no |
| *L. acidipiscis* | 1 | 3.77 | n.a. | 3.79 | n.a. | yes |
| *L. collinoides* | 1 | 6.14 | n.a. | 3.92 | n.a. | yes |
| *L. paracollinoides* | 2 | 3.49 | 3.52 | 3.82 | 0.08 | no |
| *L. coryniformis* | 5 | 2.20 | 1.65 | 3.96 | 0.05 | no |
| *L. diolivorans* | 2 | 2.06 | 1.49 | 3.90 | 0.04 | no |
| *L. hammesii* | 2 | 3.73 | 3.87 | 3.98 | 0.33 | yes |
| *L. herbarum* | 1 | 1.00 | n.a. | 3.84 | n.a. | no |
| *L. kefiranofaciens* | 1 | 1.00 | n.a. | 3.22 | n.a. | no |
| *L. kimchii* | 1 | 1.00 | n.a. | 3.92 | n.a. | no |
| *L. kisonensis* | 2 | 2.50 | 2.12 | 3.91 | 0.10 | no |
| *L. namurensis* | 5 | 3.93 | 1.69 | 3.86 | 0.08 | yes |
| *L. nodensis* | 1 | 7.27 | n.a. | 3.79 | n.a. | yes |
| *L. otakiensis* | 1 | 1.00 | n.a. | 3.72 | n.a. | no |
| *L. brevis* | 1 | 4.00 | n.a. | 3.69 | n.a. | no |
| *L. parabrevis* | 3 | 3.07 | 3.58 | 3.93 | 0.21 | no |
| *L. rapi* | 1 | 3.00 | n.a. | 4.08 | n.a. | no |
| *L. rossiae* | 2 | 4.32 | 2.55 | 4.01 | 0.04 | yes |
| *L. saniviri* | 2 | 1.00 | 0.00 | 3.93 | 0.01 | no |
| *L. senmaizukei* | 1 | 1.00 | n.a. | 4.18 | n.a. | no |
| *L. similis* | 1 | 5.45 | n.a. | 3.91 | n.a. | yes |
| *L. sunkii* | 1 | 1.00 | n.a. | 3.72 | n.a. | no |
| *L. tucceti* | 1 | 7.34 | n.a. | 3.78 | n.a. | yes |
| *L. versmoldensis* | 4 | 6.02 | 0.69 | 3.82 | 0.04 | yes |
| *L. zymae* | 6 | 4.86 | 2.01 | 3.94 | 0.11 | yes |

log cfu and pH after storage at 37° C. for 30 days obtained by assay A using strains of 33 species of *Lactobacillus*; STD: standard deviation; n.a.: not applicable As shown in Table 1 and FIGS. 1 and 2, strains of 11 *Lactobacillus* species fulfilled the two parameters defined for selection, i.e., both a viability of at least $5\times10^3$ cfu (3.69 log 10 cfu) and a pH decrease of at most 0.6 unit (i.e., a pH of at least 3.7) after storage at 37° C. for 30 days: *Lactobacillus plantarum, Lactobacillus zymae, Lactobacillus rossiae, Lactobacillus collinoides, Lactobacillus similis, Lactobacillus versmoldensis, Lactobacillus acidipiscis, Lactobacillus hammesii, Lactobacillus namurensis, Lactobacillus nodensis* and *Lactobacillus tucceti.*

Example 2: Screening of Stable Lactic Acid Bacteria (Strains)

A more in-depth study of the strains encompassed by these 11 *Lactobacillus* species was carried out, by assay A. Strains were then classified in 4 categories according to their viability and the pH of the yoghurt, after storage at 37° C. for 30 days (Table 2).

TABLE 2 classification of strains with respect to their viability and ability to decrease pH

| Classification | minimal pH value | minimal pH ΔpH | minimal cfu Log10 | minimal cfu / |
|---|---|---|---|---|
| 1 | 4 | <0.3 | 5 | $1\times10^5$ |
| 2 | 3.8 | <0.5 | 4 | $1\times10^4$ |
| 3 | 3.7 | <0.6 | 4 | $1\times10^4$ |
| 3 | 3.8 | <0.5 | 3.69 | $5\times10^3$ |
| 4 | 3.7 | <0.6 | 3.69 | $5\times10^3$ |

TABLE 3

Figure 3:
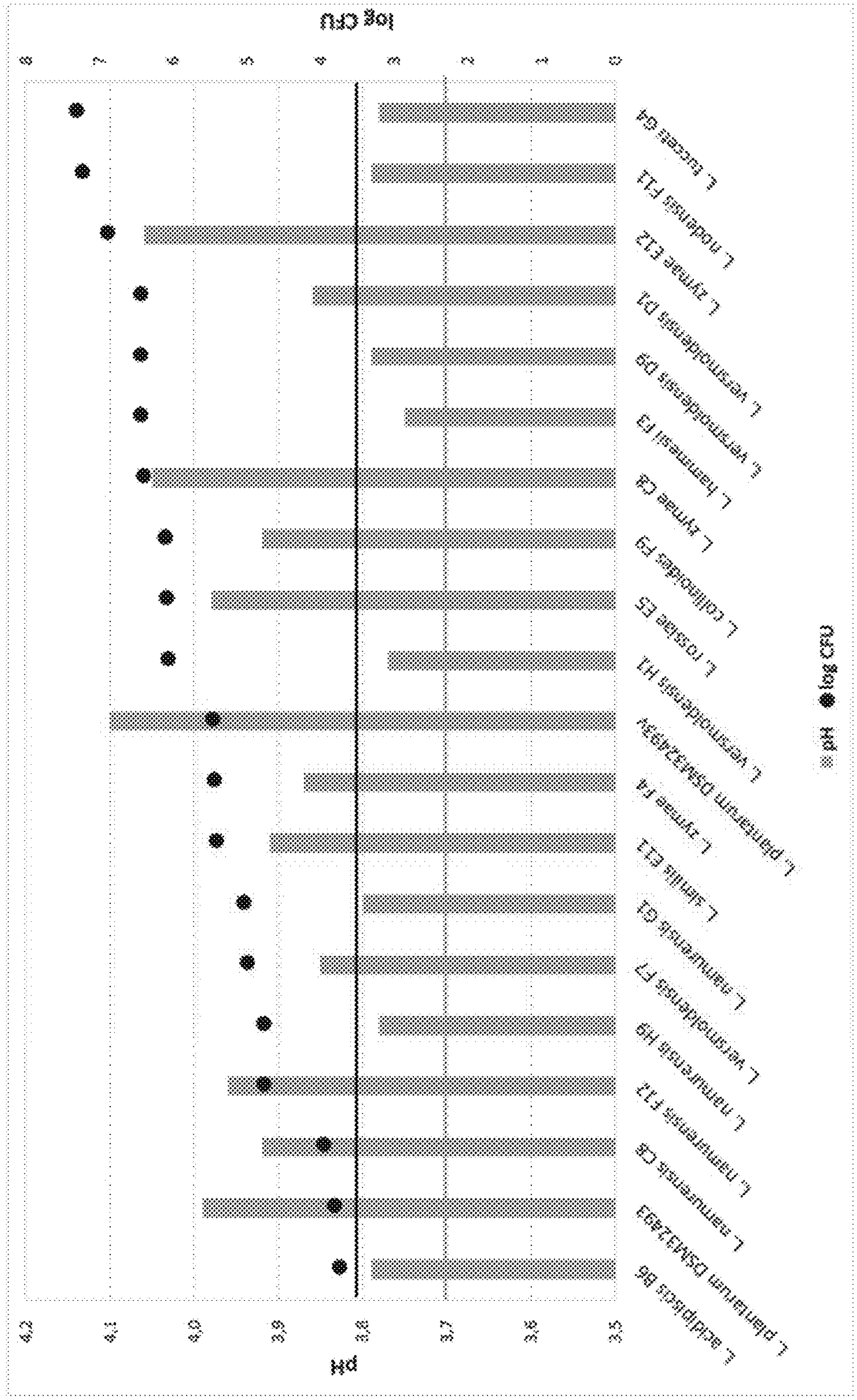
FIG. 3 is a graph showing the pH of a test yoghurt inoculated with one of the 20 tested strains (grey bars) and showing the viability (in log cfu) of the tested 20 strains in a test yoghurt (black dots), after storage for 30 days at 37° C. by assay A.

Results obtained by assay A on 20 strains is summarized in Table 3 and FIG. 3.

| Strain | log CFU | pH | classification |
|---|---|---|---|
| *L. acidipiscis* B6 | 3.8 | 3.79 | 4 |
| *L. plantarum* DSM32493 | 3.8 | 3.99 | 3 |
| *L. namurensis* C8 | 4.0 | 3.92 | 2 |
| *L. namurensis* F12 | 4.8 | 3.96 | 2 |
| *L. namurensis* H9 | 4.8 | 3.78 | 3 |
| *L. versmoldensis* F7 | 5.0 | 3.85 | 2 |
| *L. namurensis* G1 | 5.1 | 3.80 | 2 |
| *L. similis* E11 | 5.4 | 3.91 | 3 |
| *L. zymae* F4 | 5.5 | 3.87 | 2 |
| *L. plantarum* DSM32493v* | 5.5 | 4.10 | 1 |
| *L. versmoldensis* H1 | 6.1 | 3.77 | 3 |
| *L. rossiae* E5 | 6.1 | 3.98 | 2 |
| *L. collinoides* F9 | 6.1 | 3.92 | 2 |
| *L. zymae* C8 | 6.4 | 4.05 | 1 |
| *L. hammesii* F3 | 6.5 | 3.75 | 3 |
| *L. versmoldensis* D9 | 6.5 | 3.79 | 3 |
| *L. versmoldensis* D1 | 6.5 | 3.86 | 2 |
| *L. zymae* E12 | 6.9 | 4.06 | 1 |
| *L. nodensis* F11 | 7.3 | 3.79 | 3 |
| *L. tucceti* G4 | 7.3 | 3.78 | 3 |

log CFU and pH obtained using stable lactic acid bacteria after storage 30 days at 37° C.
(*DSM32493v is a variant of DSM32493 bearing the mutation G to A at position 506 of its ATP synthase alpha subunit gene as compared to DSM32493 and producing an ATP synthase alpha subunit protein as defined in SEQ ID NO: 5)

Thus, the 20 strains were classified as follows:

3 strains in category 1 (exceptionally high viability and exceptionally low pH decrease, after storage)

8 strains in category 2 (very high viability and very low pH decrease, after storage)

8 strains in category 3 (very high viability and low pH decrease, or high viability and very low pH decrease, after storage)

1 strain in category 4 (high viability and low pH decrease, after storage).

These results show that the assay A described herein enables to select strains not only maintaining a high viability in yoghurt after storage at 37° C. for 30 days, but also strains slightly decreasing the pH of this yoghurt after storage. These 20 strains are stable lactic acid bacteria suitable to manufacture a food product stable at ambient temperature.

Example 3: Manufacture of a Food Product Stable at Ambient Temperature with *L. plantarum* DSM32493

A yoghurt having the following features—2.8% protein, 3% fat, 8% sucrose; pH 4.3—was heat-treated to reduce the level of bacteria to less than $1\times10^2$ CFU per g. The DSM32493 strain (classified in category 3 according to example 2) was inoculated at a level of $1\times10^7$ cfu/ml of yoghurt.

The inoculated yoghurt was mixed, sealed and stored at 25° C. for 180 days. These conditions represent average ambient storage conditions, when food products are stored out of the fridge or out of cold rooms.

Figure 4:
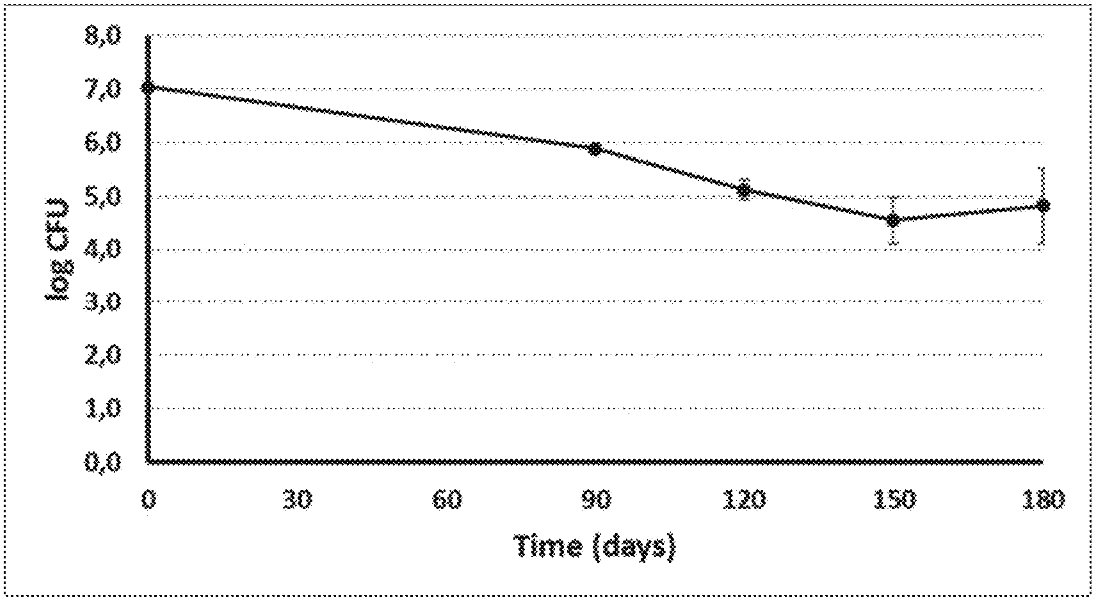
FIG. 4 is a graph showing (A) the evolution of viability (in log cfu) of the DSM32493 strain in a yoghurt and (B) the evolution of the pH of the yoghurt, during storage for 180 days at 25° C.
Figure 4:
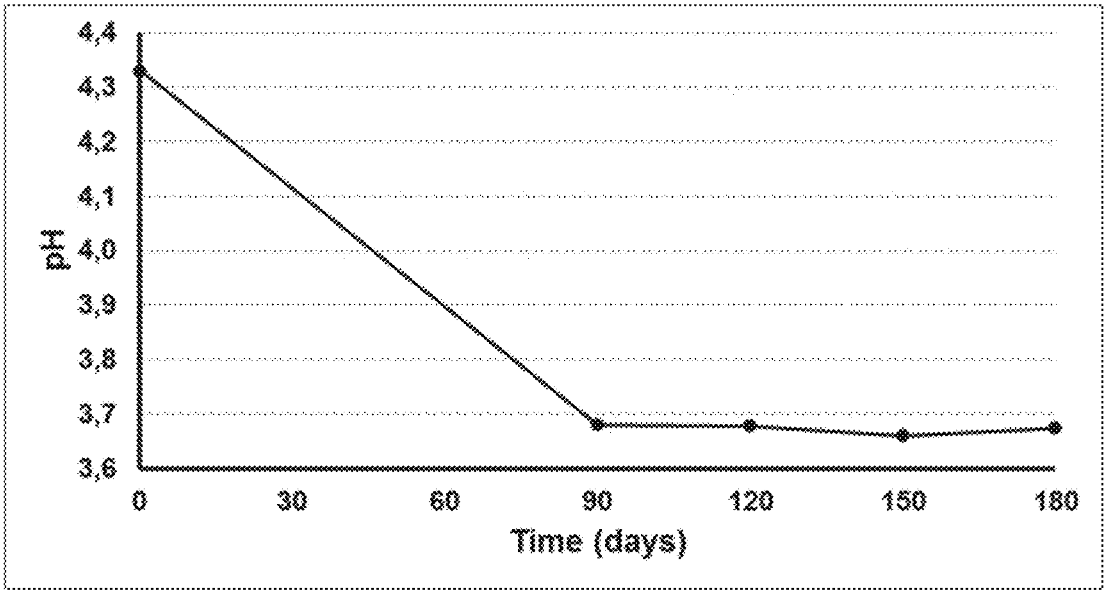

The pH and the amount of stable LAB (cell count) were determined as described for assay A above, at days 90, 120, 150 and 180. Strain viability and pH over time are represented in FIGS. 4A and 4B respectively.

The amount of DSM32493 strain after 180 days at 25° C. is 4.8 log 10 CFU, i.e., was above $1\times10^4$ cfu/g of product. This represented a decrease in the amount of bacteria which is less than 3 log, confirming that the DSM32493 can maintain a high viability after 6-month storage at ambient temperature. Interestingly, the maximal amount decrease was obtained at 150 days and slightly increased between day 150 and day 180.

The pH of the product after 180 days at 25° C. was 3.67, i.e., representing a pH decrease which is less than 0.7 unit. Interestingly, the maximal pH decrease was reached at 90 days, and was stable between day 90 and day 180.

These data confirm that the DSM32493 strain is a suitable lactic acid bacterium to manufacture food product stable at ambient temperature. This also confirm more generally that lactic acid bacteria able either to maintain a viability of $5\times10^3$ cfu/g together with a pH decrease of at most 0.5 or to maintain a viability of $1\times10^4$ cfu/g together with a pH decrease of at most 0.6 (i.e., classified in category 3) when selected by assay A, are suitable stable lactic acid bacteria to manufacture food product stable at ambient temperature

Example 4: Manufacture of a Food Product Stable at Ambient Temperature with a Variant of *L. plantarum* DSM32493 (DSM32493v)

A yoghurt having the following features—2.8% protein, 3% fat, 8% sucrose; pH 4.3—was heat-treated to reduce the level of bacteria to less than $1\times10^2$ CFU per g. A variant of the DSM32493 strain, DSM32493v (classified in category 1 according to example 2), was inoculated at a level of $1\times10^7$ cfu/ml of yoghurt. The inoculated yoghurt was mixed, sealed and stored at 25° C. for 180 days.

Figure 5:
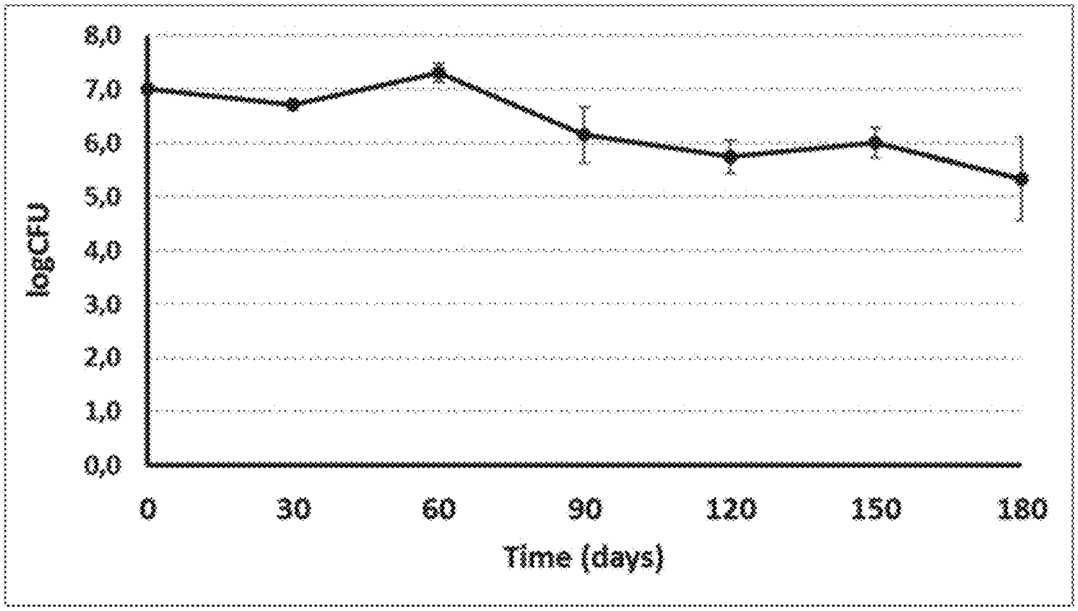
FIG. 5 is a graph showing (A) the evolution of viability (in log cfu) of the DSM32493v strain in a yoghurt and (B) the evolution of the pH of the yoghurt, during storage for 180 days at 25° C.
Figure 5:
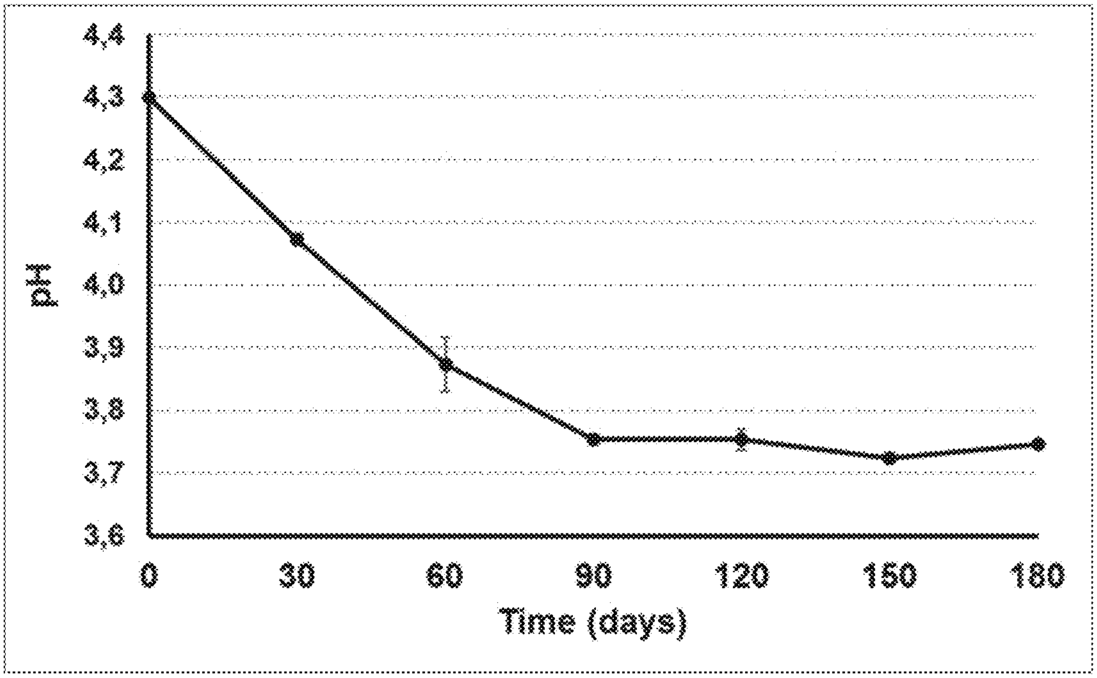

The pH and the amount of stable LAB (cell count) were determined as described for assay A above, at days 90, 120, 150 and 180. Strain viability and pH over time are represented in FIGS. 5A and 5B respectively.

The amount of DSM32493v strain after 180 days at 25° C. is 5.3 log 10 CFU, i.e., was above $1\times10^5$ cfu/g of product. This represented a decrease in the amount of bacteria which is less than 2 log, confirming that the DSM32493v can maintain a very high viability after 6-month storage at ambient temperature.

The pH of the product after 180 days at 25° C. was 3.77, i.e., representing a pH decrease which is less than 0.6 unit. Interestingly, the maximal pH decrease was reached at 90 days, and was stable between day 90 and day 180.

These data confirm that the DSM32493v strain is a suitable lactic acid bacterium to manufacture food product stable at ambient temperature. This also confirm more generally that lactic acid bacteria able to maintain a viability of $1\times10^5$ cfu/g together with a pH decrease of at most 0.3 (i.e., classified in category 1) when selected by assay A, are suitable stable lactic acid bacteria to manufacture food product stable at ambient temperature.

Altogether these data show that strains selected according to assay A as described herein are confirmed to be suitable for the manufacture of a food product stable at ambient temperature.

Example 5: Identification of Further Stable *Lactobacillus plantarum* Strains Further *L. plantarum* strains of the Dupont Danisco collection were tested by assay A, and their viability and the pH of the yoghurt, after storage at 37° C. for 30 days determined. Results for 2 *L. plantarum* strains are described in Table 4.

TABLE 4

| Strain | log CFU | pH | classification |
|---|---|---|---|
| *L. plantarum* DSM33120 | 5.4 | 4.11 | 1 |
| *L. plantarum* DSM33121 | 5.7 | 4.08 | 1 |

log CFU and pH obtained using stable *L. plantarum* strains after storage 30 days at 37° C.

The two *L. plantarum* strains identified (DSM33120 and DSM33121) show an exceptional high viability and exceptional low pH decrease, after storage, when tested by assay A, and were classified in category 1. These 2 new strains are stable lactic acid bacteria suitable to manufacture a food product stable at ambient temperature.

These results confirm that assay A described herein enables to select strains not only maintaining a high viability in yoghurt after storage at 37° C. for 30 days, but also strains slightly decreasing the pH of this yoghurt after storage.

Example 6: Manufacture of a Food Product Stable at Ambient Temperature with *L. plantarum* DSM33120 or DSM33121 Strain A yoghurt having the following features—2.8% protein, 3% fat, 8% sucrose; pH 4.3—was heat-treated to reduce the level of bacteria to less than $1\times10^2$ CFU per g. The DSM33120 or DSM33121 strain (classified in category 1 according to example 5) was inoculated at a level of $1\times10^7$ cfu/ml of yoghurt.

The inoculated yoghurt was mixed, sealed and stored at 25° C. for 180 days. These conditions represent average ambient storage conditions, when food products are stored out of the fridge or out of cold rooms. The pH and the amount of stable LAB (cell count) were determined as described for assay A above, at days 90, 120, 150 and 180.

Figure 6:
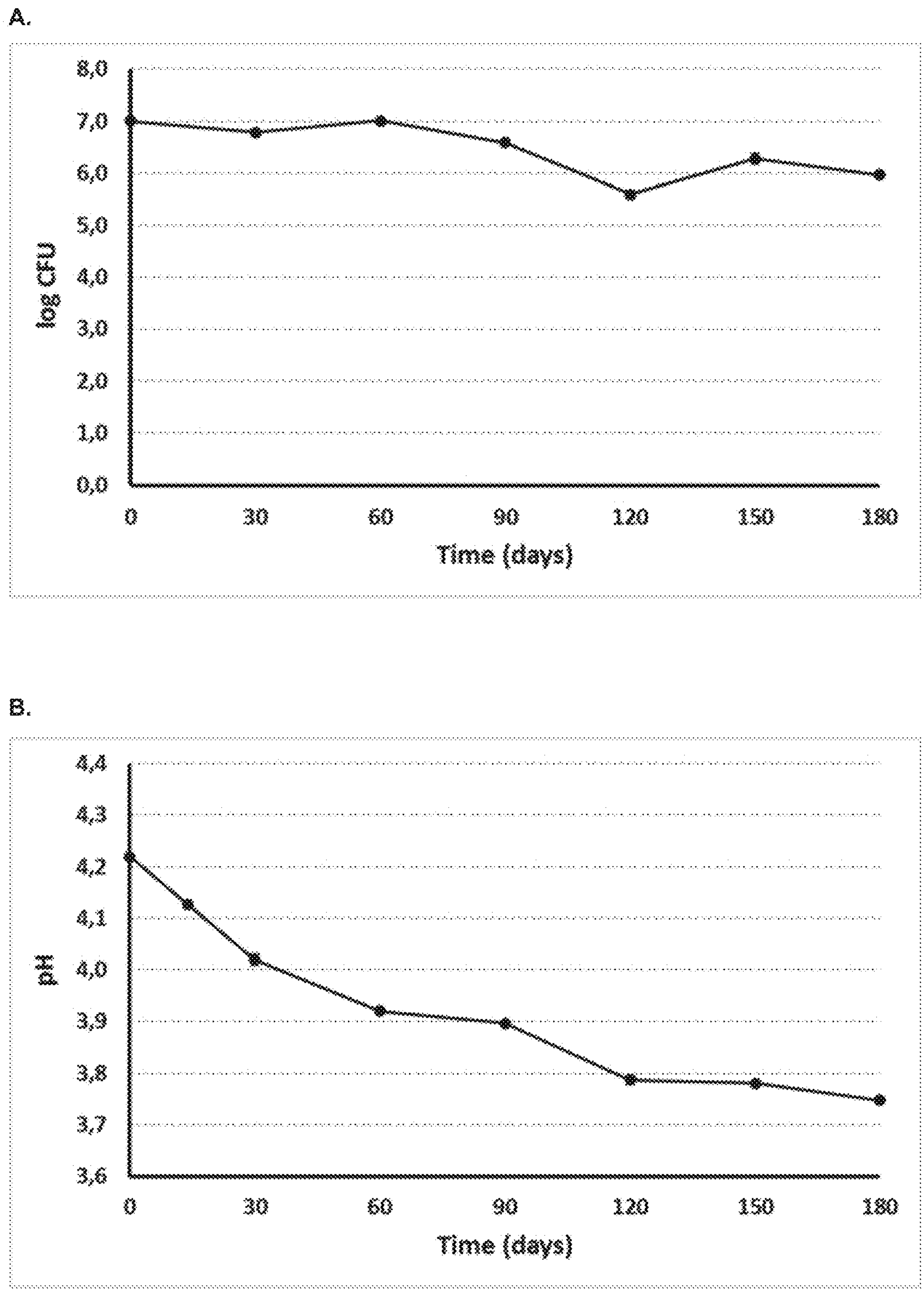
FIG. 6 is a graph showing (A) the evolution of viability (in log cfu) of the DSM33120 strain in a yoghurt and (B) the evolution of the pH of the yoghurt, during storage for 180 days at 25° C.

Strain viability and pH over time for the DSM33120 strain are represented in FIGS. 6A and 6B respectively. The amount of DSM33120 strain after 180 days at 25° C. is 5.96 log 10 CFU, i.e., was above $9\times10^5$ cfu/g of product. This represented a decrease in the amount of bacteria of about 1 log, confirming that the DSM33120 can maintain a very high viability after 6-month storage at ambient temperature. The pH of the product after 180 days at 25° C. was 3.75, i.e., representing a pH decrease which is less than 0.5 unit.

Figure 7:
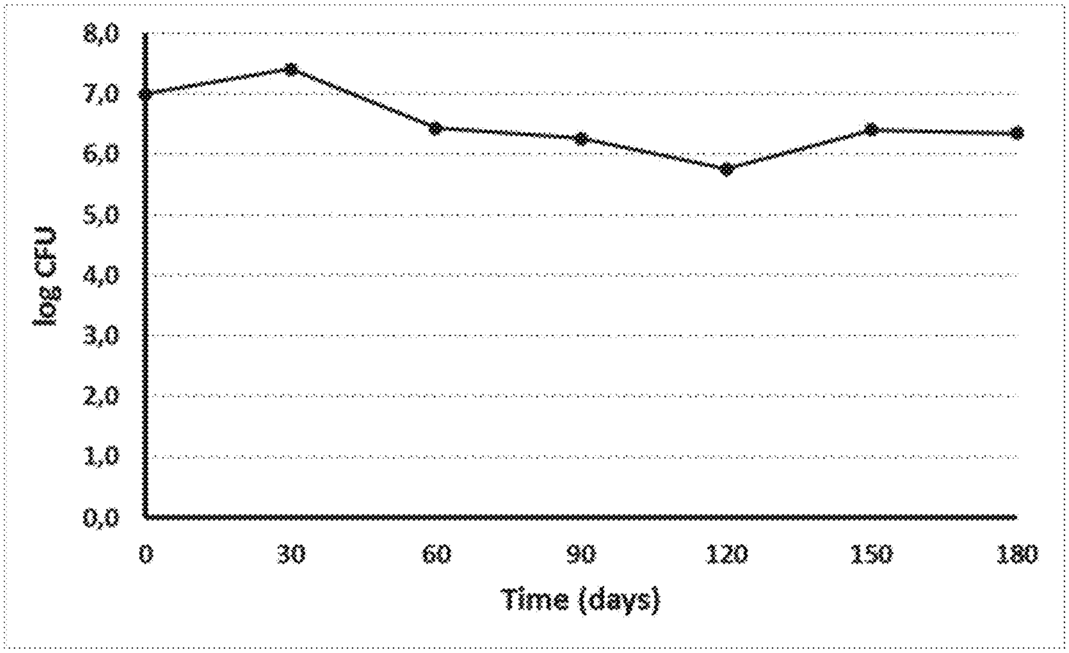
FIG. 7 is a graph showing (A) the evolution of viability (in log cfu) of the DSM33121 strain in a yoghurt and (B) the evolution of the pH of the yoghurt, during storage for 180 days at 25° C.
Figure 7:
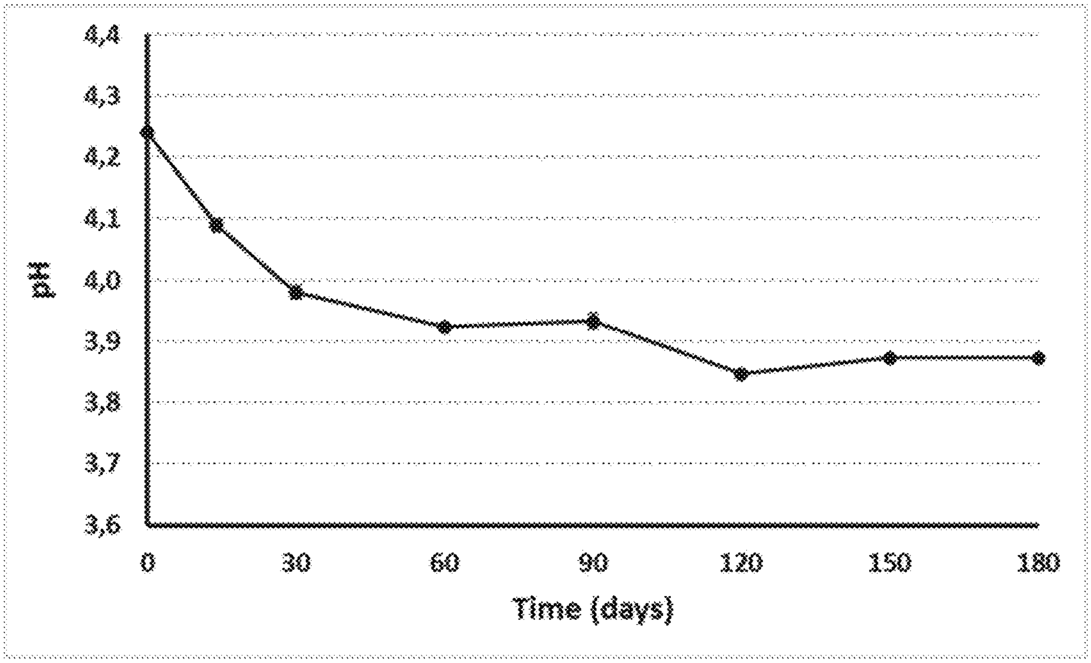

Strain viability and pH over time for the DSM33121 strain are represented in FIGS. 7A and 7B respectively. The amount of DSM33121 strain after 180 days at 25° C. is 6.35 log 10 CFU, i.e., was above $2\times10^6$ cfu/g of product. This represented a decrease in the amount of bacteria which is less than 0.7 log, confirming that the DSM333121 can maintain a very high viability after 6-month storage at ambient temperature. The pH of the product after 180 days at 25° C. was 3.87, i.e., representing a pH decrease which is less than 0.4 unit.

These data confirm that the DSM33120 and DSM33121 strains are suitable lactic acid bacteria to manufacture food product stable at ambient temperature. This also confirm more generally that lactic acid bacteria able either to maintain a viability of $1\times10^5$ cfu/g together with a pH decrease of at most 0.3 (i.e., classified in category 1) when selected by assay A, are suitable stable lactic acid bacteria to manufacture food product stable at ambient temperature.

The invention claimed is:

1. A process for manufacturing a food product stable at an ambient temperature of 25° C., said process comprising screening for and identifying strains capable of generating a food product stable at an ambient temperature of 25° C., wherein the process comprises adding to an initial food product with a pH of between 3.4 and 4.6, and containing a level of bacteria which is no more than $1\times10^2$ CFU per g, one or more stable lactic acid bacteria in a total amount of at least $1\times10^5$ CFU per g, to obtain a food product stable at an ambient temperature of 25° C., wherein:

(i) each of said one or more stable lactic acid bacterium is selected from a strain of the species *Lactobacillus plantarum*; and (ii) each of said one or more stable lactic acid bacterium, when added in an amount of $1\times10^7$ CFU per g to a test yoghurt having a pH of 4.3, previously heat-treated at 75° C. for 25 seconds:

a) retains viability in an amount of at least $5\times10^3$ CFU/g after storing said test yoghurt 30 days at a temperature of 37° C.; and b) decreases the pH of said test yoghurt by at most 0.6 units after storing said test yoghurt 30 days at a temperature of 37° C., wherein the strain of the species *Lactobacillus plantarum* is selected from the group consisting of the strain DSM32493 deposited at the DSMZ on Apr. 26, 2017, the strain DSM33120 deposited at the DSMZ on May 22, 2019, the strain DSM33121 deposited at the DSMZ on May 22, 2019, and a variant of the DSM32493 strain into which the ATP synthase alpha subunit gene of the ATP-synthase operon bears the mutation G to A at its position 506; and wherein the food product is stable at ambient temperature after storing it for 180 days at a temperature of 25° C.

2. The process according to claim 1, wherein said one or more stable lactic acid bacterium when added in an amount of $1\times10^7$ CFU per g to a test yogurt having a pH of 4.3, previously heat-treated at 75° C. for 25 seconds, retains viability in an amount of at least $1\times10^4$ CFU/g after storing said test yoghurt 30 days at a temperature of 37° C.

3. The process according to claim 1, wherein said one or more stable lactic acid bacterium, when added in an amount of $1\times10^7$ CFU per g to a test yogurt having a pH of 4.3, previously heat-treated at 75° C. for 25 seconds decreases the pH of said test yoghurt by at most 0.5 units after storing said test yoghurt 30 days at a temperature of 37° C.

4. The process according to claim 1, wherein said initial food product with a pH of between 3.4 and 4.6 is selected from the group consisting of a fermented dairy product, a chemically-acidified dairy product, a fruit juice, a fermented juice, a vegetable juice, a fermented vegetable juice, a chemically-acidified cereal product, a fermented cereal product, a chemically-acidified rice product, a fermented rice product, a chemically-acidified nut product, a fermented nut product, a fermented soy milk product, and any mixture thereof.

5. The process according to claim 1, wherein said initial food product with a pH of between 3.4 and 4.6 is a fermented dairy milk product.

6. The process according to claim 1, wherein said initial food product with a pH of between 3.4 and 4.6 is treated so as to obtain an initial low bacteria-containing food product comprising a level of bacteria which is no more than $1\times10^2$ CFU per g of said initial low bacteria-containing food product.

7. The process according to claim 6, wherein said initial low bacteria-containing food product is a fermented dairy milk product.

8. The process according to claim 1, wherein the pH of said initial food product is between 3.4 and 4.0, between 4.0 and 4.6 or between 3.6 and 4.2.

9. The process according to claim 1, wherein said one or more stable lactic acid bacteria are added to the initial food product in a total amount of at least $5\times10^5$ per g.

10. The process according to claim 1, wherein said one or more stable lactic acid bacteria are added aseptically to the initial food product.

11. The process according to claim 1, wherein the variant when added in an amount of $1\times10^7$ CFU per g to a test yoghurt having a pH of 4.3, previously heat-treated at 75° C. for 25 seconds a) retains viability in an amount of at least $5\times10^3$ CFU/g after storing said test yoghurt 30 days at a temperature of 37° C.; and b) decreases the pH of said test yoghurt of at most 0.6 units after storing said test yoghurt 30 days at a temperature of 37° C.

12. The process according to claim 1, wherein the food product is stable when the amount of stable lactic acid bacteria it contains is at least $1\times10^5$ CFU/g and is not decreased more than 3 log.

13. The process according to claim 1, wherein the initial food product is a yoghurt.

* * * * *